(12) United States Patent
Krueger et al.

(10) Patent No.: US 9,468,807 B1
(45) Date of Patent: Oct. 18, 2016

(54) SYSTEMS, APPLICATIONS, AND METHODS FOR EXERCISE WORKOUT GENERATION

(71) Applicant: Fit Intuition, LLC, Reno, NV (US)

(72) Inventors: Ryan M. Krueger, Reno, NV (US); Lee Huber, Reno, NV (US); Ralph Krueger, Reno, NV (US)

(73) Assignee: Fit Intuition, LLC, Reno, NV (US)

( * ) Notice: Subject to any disclaimer, the term of this patent is extended or adjusted under 35 U.S.C. 154(b) by 0 days.

(21) Appl. No.: 14/641,367

(22) Filed: Mar. 7, 2015

Related U.S. Application Data

(63) Continuation of application No. 14/512,928, filed on Oct. 13, 2014.

(60) Provisional application No. 61/890,035, filed on Oct. 11, 2013.

(51) Int. Cl.
 *G09B 7/00* (2006.01)
 *A63B 24/00* (2006.01)
(52) U.S. Cl.
 CPC .................. *A63B 24/0075* (2013.01)
(58) Field of Classification Search
 CPC ....................................................... G06F 17/60
 USPC ............................................. 434/247; 705/10
 See application file for complete search history.

(56) References Cited

U.S. PATENT DOCUMENTS

| | | | | |
|---|---|---|---|---|
| 7,130,680 | B2 * | 10/2006 | Kodama et al. | 600/547 |
| 8,066,514 | B2 * | 11/2011 | Clarke | A63B 24/00 434/236 |
| 2002/0013521 | A1 * | 1/2002 | Baba et al. | 600/301 |
| 2002/0040195 | A1 * | 4/2002 | Takehara et al. | 600/551 |
| 2004/0044560 | A1 * | 3/2004 | Giglio et al. | 705/10 |
| 2005/0240444 | A1 * | 10/2005 | Wooten et al. | 705/3 |
| 2006/0136173 | A1 * | 6/2006 | Case, Jr. | A63B 24/00 702/182 |
| 2006/0217600 | A1 * | 9/2006 | Lee et al. | 600/300 |
| 2007/0219059 | A1 * | 9/2007 | Schwartz | A61B 5/0205 482/8 |
| 2008/0077619 | A1 * | 3/2008 | Gilley | G06Q 30/02 |
| 2008/0228520 | A1 * | 9/2008 | Day et al. | 705/2 |
| 2008/0312040 | A1 * | 12/2008 | Ochi et al. | 482/8 |
| 2009/0253554 | A1 * | 10/2009 | McIntosh | A63B 21/00 482/4 |
| 2010/0216601 | A1 * | 8/2010 | Saalasti | A61B 5/024 482/8 |
| 2010/0267521 | A1 * | 10/2010 | Matsunaga | A63B 24/0075 482/9 |
| 2011/0201476 | A1 * | 8/2011 | Solomon | A63B 24/0062 482/8 |
| 2012/0203092 | A1 * | 8/2012 | Sweeney et al. | 600/390 |
| 2013/0095459 | A1 * | 4/2013 | Tran | 434/247 |

* cited by examiner

*Primary Examiner* — Sam Yao
*Assistant Examiner* — Alvin Carlos
(74) *Attorney, Agent, or Firm* — D.C. Williams

(57) ABSTRACT

In some embodiments, an automated system comprises one or more biometric sensors, an interactive screen, and an exercise routine generation application communicable with a mobile application. In some embodiments, the mobile application receives data from an automated station and displays exercise routines, other exercise information, or both. In some embodiments, the mobile application includes a scanner to scan labels, other indicia, or physical or other features of an exercise machine or other exercise apparatus to identify the machine or apparatus. In some embodiments, the mobile application communicates with one or more local or remote databases identifying differing exercise facility locations within a geographic area and identifying exercise apparatus available in each of the differing facilities.

20 Claims, 20 Drawing Sheets

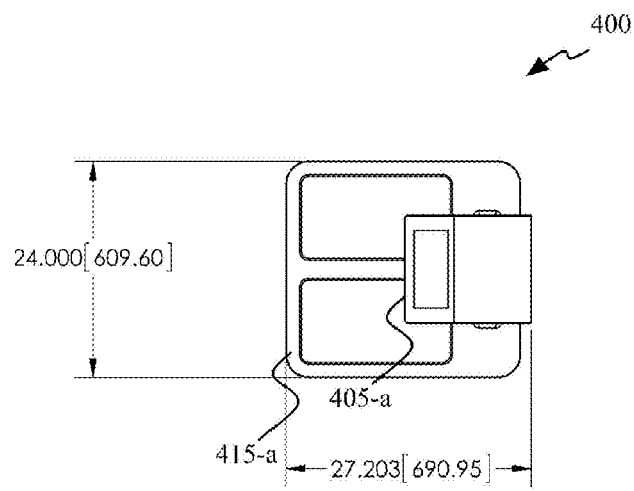
Figure 5
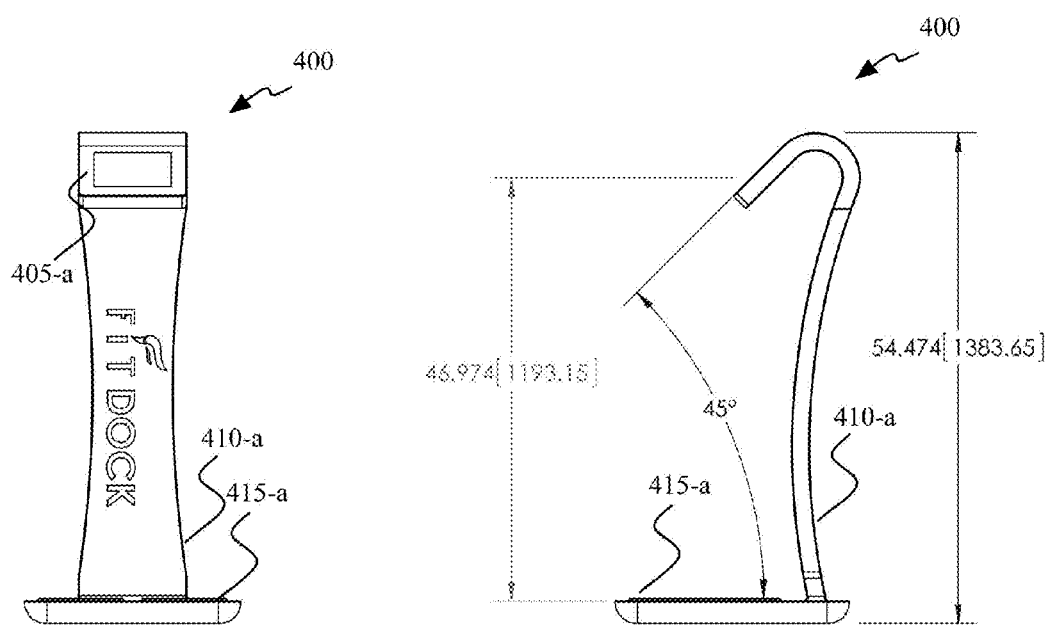
Figure 6
Figure 7

US 9,468,807 B1

SYSTEMS, APPLICATIONS, AND METHODS FOR EXERCISE WORKOUT GENERATION

CROSS-REFERENCE TO RELATED APPLICATIONS

This application is a Continuation of pending U.S. Nonprovisional patent application Ser. No. 14/512,928 entitled "Biosensing Systems, Applications, and Methods" filed on Oct. 13, 2014, which application claims benefit of U.S. Provisional Patent Application No. 61/890,035, also entitled "Biosensing Systems, Applications, and Methods" and filed on Oct. 11, 2013. The instant application claims benefit of, and incorporates herein by reference in their entireties for all useful purposes, both of the applications above (Ser. Nos. 14/512,928 and 61/890,035). In the event of any inconsistency between the prior patent applications and the instant application (including without limitation any limiting aspects), the instant application shall prevail.

COPYRIGHT NOTICE

This patent document contains material subject to copyright protection. The copyright owner has no objection to the photocopy reproduction of the patent document or the patent disclosure in exactly the form it appears in the Patent and Trademark Office patent file or records, but otherwise reserves all copyright rights.

FIELD OF DISCLOSURE

The present disclosure relates to an automated system that utilizes information from and about users to generate personalized exercise workout information.

BACKGROUND

Biometric sensor systems are old in the art. A prior Internet publication regarding a Tanita "MC-980 Multi Frequency Segmental Body Composition Meter" (the "Tanita reference") describes a biosensor information collection system having a automated stand/station with a scale at the base of the stand and a digital display at the top of the stand. The publication further explains that a height measurement accessory is optional.

The system disclosed in the Tanita reference is not an exercise development system. For example, the system as disclosed in the Tanita reference does not provide any exercise recommendations, much less do so by identifying specific exercises to be performed on identified exercise equipment. The system of the Tanita reference also does not connect with a mobile application that may be utilized to collect data about specific exercise apparatus or specific exercise facilities. There are many other aspects of the present disclosure not disclosed in the Tanita reference.

Mobile exercise development applications have also been disclosed in the prior art. One such reference, U.S. Published Patent Application No. 20130196821 (the '821 reference), discloses a mobile exercise development application that collects biometric information about a user, collects data about available exercise machines (such as with a scanner on the mobile device), and, with both of these types of information, generates customized exercise routines for the user.

The '821 reference does not disclose an automated biometric information collection station much less use of such a stand to provide the biometric data to a mobile exercise development application. The '821 reference also does not disclose use of information generated by the application, such as exercise apparatus identification data for apparatus in particular locations, to provide a database of exercise apparatus at differing such locations.

Further, to applicants' knowledge, the prior art does not include any such database compilation of exercise facilities by location much less one accessible by a mobile application. Although Google maps and other mobile applications have long tracked and reported a mobile device user's location and directions to differing identified locations, to applicants' knowledge such prior art applications have not provided an identification of differing exercise facility locations along with identification of exercise resources, such as particular machines, available at the locations respectively. Similarly, they have not provided automatic identification of the subset of locations available locally to a mobile application/device user. And, mapping features have not been provided with any such features to applicants' knowledge.

SUMMARY OF SOME ASPECTS OF THIS SPECIFICATION

The applicants believe they have discovered problems and deficiencies in the prior art such as those set forth above and others solved by one or more embodiments disclosed in this specification.

In one aspect, the present specification is directed to an automated system having one or more biometric sensors, an interactive screen, and an exercise routine generation application. In some embodiments, the automated system further comprises and is communicable with a mobile application that can receive data from the automated system and display exercise routines or other exercise information to a user. In some embodiments, the mobile application can include a scanner to scan labels, other indicia, or physical or other features of an exercise machine or other exercise apparatus to identify the machine or apparatus. In some systems, the automated system comprises an automated station including a support arm extending from a weighing scale to the interactive screen supported by the support arm.

In another aspect, this specification discloses a mobile application that communicates with local or remote one or more databases to identify differing exercise facility locations within a geographic area and identify exercise apparatus available in each of the differing facilities. In some systems, the mobile application/device can include a scanner such as identified above to identify exercise resources available a given facility and place that information into the one or more databases.

In certain embodiments, users can access exercise facility information through their mobile devices. For example, a mobile application can procure the user's location through GPS monitoring and procure and display local exercise facilities and their respective exercise resources.

In certain embodiments, the automated system or an automated station is communicable with the mobile application that reports differing exercise facilities and exercise apparatus available in the differing facilities. The mobile application/device can include a scanning feature such as set forth above. In some embodiments, the mobile application or web or other portal can provide the user with locations of exercise facilities that have equipment, such as the automated station, compatible with the user's mobile application or that the user can use to otherwise access the user's information provided earlier such as, for example, for storage in one or more databases. Some systems can include all the features identified above. Additional features of the automated system, automated station, or mobile application include instructions for how to perform an exercise and/or graphic or video demonstrations of exercises with identified apparatus.

In some embodiments, the automated station can act as a personal trainer that generates workout recommendations, video tutorials, and specific body group exercises. For example, the automated station can provide the ability to help patrons of small un-managed gymnasiums by providing a step-by-step guide for fitness instruction.

In some embodiments, the automated station can report damaged equipment to managers, etc. The automated station also can communicate with an optional mobile phone application that offers a handheld guide to user. The station can further provide a complete resource for small to large gymnasium/complex utilization.

In some embodiments, the automated station and mobile application (such as an iPhone, iPad, iPod, or smartphone mobile application) may each include at least one of any of a login to keep track of body stat information (weight, fat percentage, muscle mass, physique, etc), a nutrition guide, a customized periodic workout regimen for a user with adaptation when needed for a user using differing types of equipment (either in the same facility or in varying types of exercise facilities), user workout tracking data collection and reporting, video or graphical tutorials on equipment use; and GPS capabilities to locate an apartment or other exercise facility in a particular geographic local, in some embodiments with a map layout of the facility and identification of exercise resources in the gym.

With an integrated system including the automated station and the mobile application/device having user location tracking, mapping, and exercise resource identification features, a user can travel and yet easily locate and follow mapping instructions to find a suitable exercise facility if available in the user's geographic locale.

In some embodiments, the mobile application/device may also include at least one of any of a QR code scanner function for scanning and identifying exercise (or other) resources in the exercise facility, safety information, means to submit damage reports to complex manager, means to communicate with or find partners in the same facility, means to chat in linked forums about workouts and health matters, and means contact a facility manager about concerns.

Systems disclosed herein can provide novel methods of using the systems, including novel business methods. For example, one novel business method can involve utilizing a mobile application to generate database(s) identifying the types of exercise apparatus available in each of differing exercise facilities. Remuneration can then be charged for access to this data or for providing the data to users of mobile devices. Advertising in conjunction with these services can also provide a source of remuneration.

It can thus be seen that the present systems can provide one or more of the problem solutions and advantages noted above. Further, the automated station and mobile application provide increased effectiveness, safety, function, and use of the exercise facilities in differing apartment complexes, hotels, exercise clubs, or gymnasiums. With such systems, users need not wander around exercise facilities with no understanding of how to use equipment or how to develop an effective workout plan.

Other features can be included, and they will become apparent as this specification proceeds.

BRIEF DESCRIPTION OF THE DRAWINGS

The applicants' preferred and other embodiments are disclosed in association with the accompanying figures. In the figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 5 is an elevation view of the automated station of FIG. 4.

FIG. 6 is a front plan view of the automated station of FIG. 4.

FIG. 7 is a side plan view of the automated station of FIG. 4.

DETAILED DESCRIPTION OF SOME EMBODIMENTS

Figure 1:
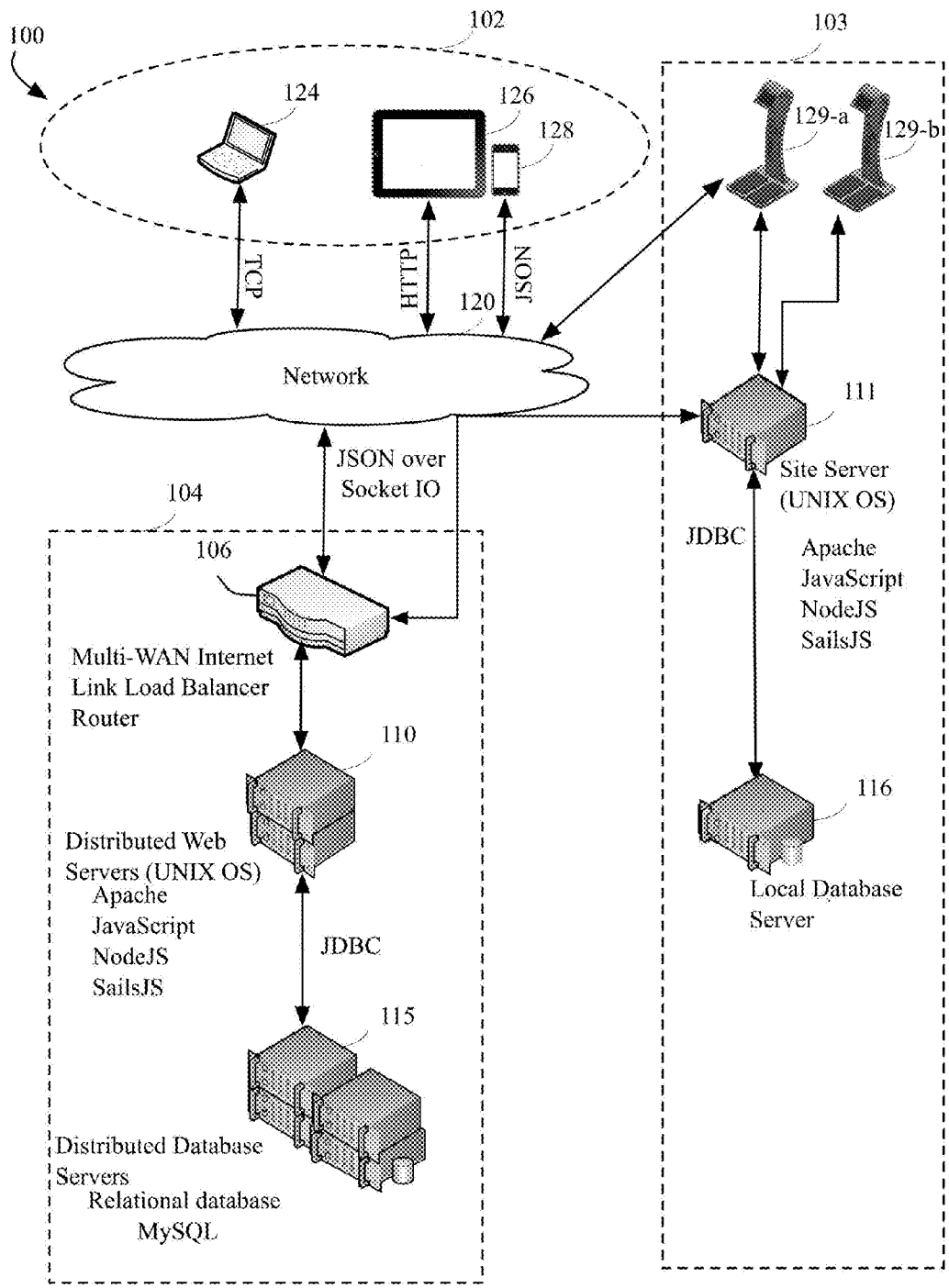
FIG. 1 is a computer network or similar digital processing environment in which an automated system can be implemented according to exemplary embodiments disclosed herein.

The following description provides examples and is not limiting of the scope of this application. Changes may be made in the function and arrangement of elements discussed without departing from the spirit and scope of the disclosure. Various embodiments may omit, substitute, add, and mix and match various procedures or components as appropriate or desired. For instance, the methods disclosed may be performed in an order different from that described and various steps may be added, omitted, or combined. Also, features disclosed with respect to certain embodiments may be combined in or with other embodiments as well as features of other embodiments.

Certain embodiments of the automated systems and methods are described with reference to methods, apparatus (systems), and computer program products that can be implemented by computer program instructions. These computer program instructions can be provided to a processor of a one or more computing devices, such as a general purpose computer, special purpose computer, mobile computing device, or other programmable data processing apparatus to produce a particular machine, such that the instructions, which execute via the processor of the computing device, implement the acts specified herein to transform data from a first state to a second state, transmit data from one computing device to another computing device, and generate physical state transitions at one or more geographic locations.

These computer program instructions can be stored in a computer-readable memory that can direct a computing device or other programmable data processing apparatus to operate in a particular manner, such that the instructions stored in the computer-readable memory produce an article of manufacture including instructions for implementing the acts specified herein. The computer program instructions may also be loaded onto a computing device or other programmable data processing apparatus to cause a series of operational steps to be performed on the computing device or other programmable apparatus to produce a computer-implemented process such that the instructions which execute on the computer or other programmable apparatus provide steps for implementing the acts specified herein.

The programming of the programmable apparatus creates a new machine, creating a special purpose computer once it is programmed that performs particular functions pursuant to instructions from program software. The automated systems can be described in terms of a dedicated circuit or a process that emulates that circuit. The software processes of the extended package collaboration system are, at least in part, interchangeable with a hardware circuit. This new machine can thus be implemented as a complex array of hardware circuits, programming that facilitates the unique functions of the extended package collaboration system, or both.

Various illustrative logical blocks, modules, and algorithm steps described in connection with the embodiments disclosed herein can be implemented as electronic hardware, computer software, or combinations of both. To illustrate this interchangeability of hardware and software, various illustrative components, blocks, modules, and steps have been described generally in terms of their functionality. Whether such functionality is implemented as hardware or software depends upon the particular application and design constraints imposed on the overall system. The described functionality can be implemented in varying ways for each particular application and function, but such implementation decisions should not be interpreted as causing a departure from the scope of the disclosure.

The various illustrative logical blocks and modules described in connection with the embodiments disclosed herein can be implemented or performed with a general purpose processor, a specific purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any conventional processor, controller, microcontroller, or state machine. A processor can also be implemented as a combination of computing devices such as, for example, a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a computer terminal. In the alternative, the processor and the storage medium can reside as discrete components in a computer terminal.

Depending on the embodiment, certain acts, events, or functions of any of the methods described herein can be performed in a different sequence, or can be added, merged, or left out altogether (e.g., not all described acts or events are necessary for the practice of the method). Moreover, in certain embodiments, acts or events can be performed concurrently such as, for example, through multi-threaded processing, interrupt processing, or multiple processors or processor cores, rather than sequentially. Moreover, in certain embodiments, acts or events can be performed on alternate tiers or on alternate components within the architecture.

In some embodiments, the system includes several components, such as, for example, a web application including a presentation layer in communication with a server-side logic layer, and a cloud-based database environment employing structured data, such as, for example, SQL defined data structures. In some implementations, one or more components are deployed on a Microsoft®, Linux®, or UNIX® operating system, such as, for example, Windows®, Ubuntu Linux®, or Mac OS X®. One or more languages can be use to implement the various components across the various architecture layers. Languages and frameworks can include, but are not limited to PHP, HTML, CSS, JavaScript, Ruby on Rails, Grails, and SQL.

Communication within systems may include standard web protocols such as, for example, HTTP/HTTPS via standard network protocols such as TCP/IP. Alternative web protocols for intra-system and Internetwork communication currently under development including HTTP version 2.0, HTTPS version 2.0, and SPDY are contemplated and within the scope of this disclosure. Successors to these protocols are also envisioned and are supported within the scope of this disclosure.

Referring now to FIG. 1, in some embodiments, a computer network or similar digital processing environment 100 supports implementation of the of the automated systems disclosed. Portions of the present systems and methods can also run on different architectures that include a LAN, WAN, stand-alone PC, stand-alone mobile device, one or more stand-alone, clustered, or networked mini or mainframe computers, etc. The automated systems can be distributed on multiple computers and devices 102, 103, 104.

FIG. 1 is representative of many specific computing arrangements that can support the automated systems and methods disclosed. In one embodiment, the software implementing the automated systems runs in the Linux® environment on an i686 architecture. In another embodiment, the software is implemented to run in other environments, such as Windows® or UNIX®, and to run on any hardware having enough power to support timely operation of software such as that identified in FIG. 1. In some implementations of the automated systems, a Linux® distribution, such as, for example, Ubuntu®, is deployed on one or more server computers 110, 111, 115, 116. In some embodiments, computers are deployed as virtual instances rather than physical computers.

In some instances, an automated station 129-*a*, 129-*b* is implemented, in part, as a combination of proprietary and off-the-shelf hardware and software. The hardware can include, for example, a standard Wi-Fi enabled Android tablet that is Android USB Accessory mode compatible. Custom hardware can include sensors configured to obtain various biological statistics, such as, for example, heart rate, body fat percentage, weight, and the like. In some implementations, the custom hardware also acts as the USB host in accordance with Android's Open Accessory Protocol. Software can include Android OS version 4.0.3, a custom Java-based Android application maintaining a SocketIO socket to the site-specific slave server 111 using an IP address and Port Number read from a config file stored on the Tablet's internal SD card, and a GUI using UnityPlayer.SendMessage method and a Unity-based graphical user interface application. In some instances, the user directly interacts with on screen elements through the Unity layer. This layer will receive messages from the Android application and then display the contents of the messages. When the user wants to perform an action that would result in data being updated, deleted, or created, the Unity layer collects the information for the change and sends it to the Android application, which then relays it to the site-specific slave server 111. In certain instances, the system can be integrated with off-the-shelf hardware and software services, such as obtaining, for example, weight and body fat percentages detected by a Fitbit Aria scale via a web services API accessing hosted Fitbit content.

A load balancing router 106, such as for example a Peplink® Multi Wan Router, can distribute traffic inside a firewall to and from distributed web servers 110. In some deployments, these webservers 110 are distributed instances of one or more application servers with distributions of Apache, a JavaScript runtime environment, Node.JS running SailsJS, along with supporting libraries such as those configured for communicating with persistent data stores, such as through a REST API. The distributed web servers 110 are communicatively coupled to computers 115 hosting one or more persistent data stores, file stores, or both. The data store can be distributed relational databases such as, for example, MySQL® 5.1.70, SQL Server®, or Oracle® storing primary and derivative data, or alternatively, can be relational databases in combinations with file stores that use native file systems. In an example, a distributed web server 110 may communicate with a distributed database server 115 via Java Database Connectivity (JDBC), Open Database Connectivity (ODBC), or other database communication protocol supported by the data store. In addition, or alternatively, the distributed database servers 115 may host XML databases, object oriented databases, NoSQL database, key-value caches and stores, and the like.

Client devices of various types 102 can connect to a remote server infrastructure 104 via a network 120 over one or more communication protocols. All computers can pass information as unstructured data, structured files, structured data streams such as, for example, XML, structured data objects such as, for example, JSON objects, and/or structured messages. Client devices 124, 126, 128 may communicate over various protocols such as, for example, UDP, TCP/IP, HTTPS and/or HTTP. In some cases, one or more client devices 124, 126, 128 may communicate via a wireless connection with the network 120.

Client computers and devices 124, 126, 128 and server computers 110, 115 provide processing, storage, and input/output devices executing application programs. Client devices 102 can also be linked through communications network 120 to other computing devices, including other client devices/processes 102 and server computers 110, 115. In some embodiments, server computers 115 host and execute software implementing centralized persistent data storage and retrieval. The network 120 can be a local area network and/or a wide area network that is part of a remote access network, a global network (e.g., the Internet), a worldwide collection of computers, and/or gateways that currently use respective protocols (TCP/IP, UDP, etc.) to communicate with one another.

Multiple client computer devices 102 can each execute and operate instances of the apps or applications accessing the automated system. In some embodiments, mobile apps provide the same functionality as applications running on the automated station excluding any hardware-related biological statistical information collection functions. The mobile app can also contain functionality locating exercise facilities based on the current location of the device running the mobile app, a selected location, or both. Additional functions can include the ability to edit a user profile, view past routines, view workouts, and track goal progress. In certain implementations an HTML browser interface is made available by one or more web servers, e.g., 110, for display on client devices 102.

On reading this disclosure, those of skill in the art will recognize that many of the components discussed as separate units may be combined into one unit and an individual unit may be split into several different units. Further, the various functions could be contained in one computer or distributed over several networked computers and/or devices. The identified components may be upgraded and replaced as associated technology improves and advances are made in computing technology.

In some embodiments, the automated systems are distributed across centralized master servers 110, 115 and site-specific slave servers 111, 116. The centralized master servers can store user profiles, as well as master copies of one or more database tables (see e.g., FIG. 3A through FIG. 3H). Site-specific slave servers 111, 116 can consist of a local implementation of some or all of the workout generation logic of the centralized master server 110. Automated stations 129-*a*, 129-*b* located at the specific site can access the site-specific slave server 111 to obtain information such as, for example, user profile data. In some instances, the site-specific slave server 111 generates workouts and modifies existing workouts locally without communicating with the centralized master server 110. The site-specific slave servers 116 may store complete copies, partial copies, or both of database tables thus reducing the amount of inbound and outbound data traffic. In some instances, some or all local database table copies are read only and are updated using a replication scheme, such as snapshot replication.

Any changes originating at the site-specific slave servers 111, 116 or the automated stations 129-a, 129-b are either redirected to the centralized master servers with the site-specific local servers re-synced, or alternatively, are stored on the site-specific local server and later synced through a synchronization mechanism capable of resolving conflicts, such as database integrity conflicts.

Figure 2:
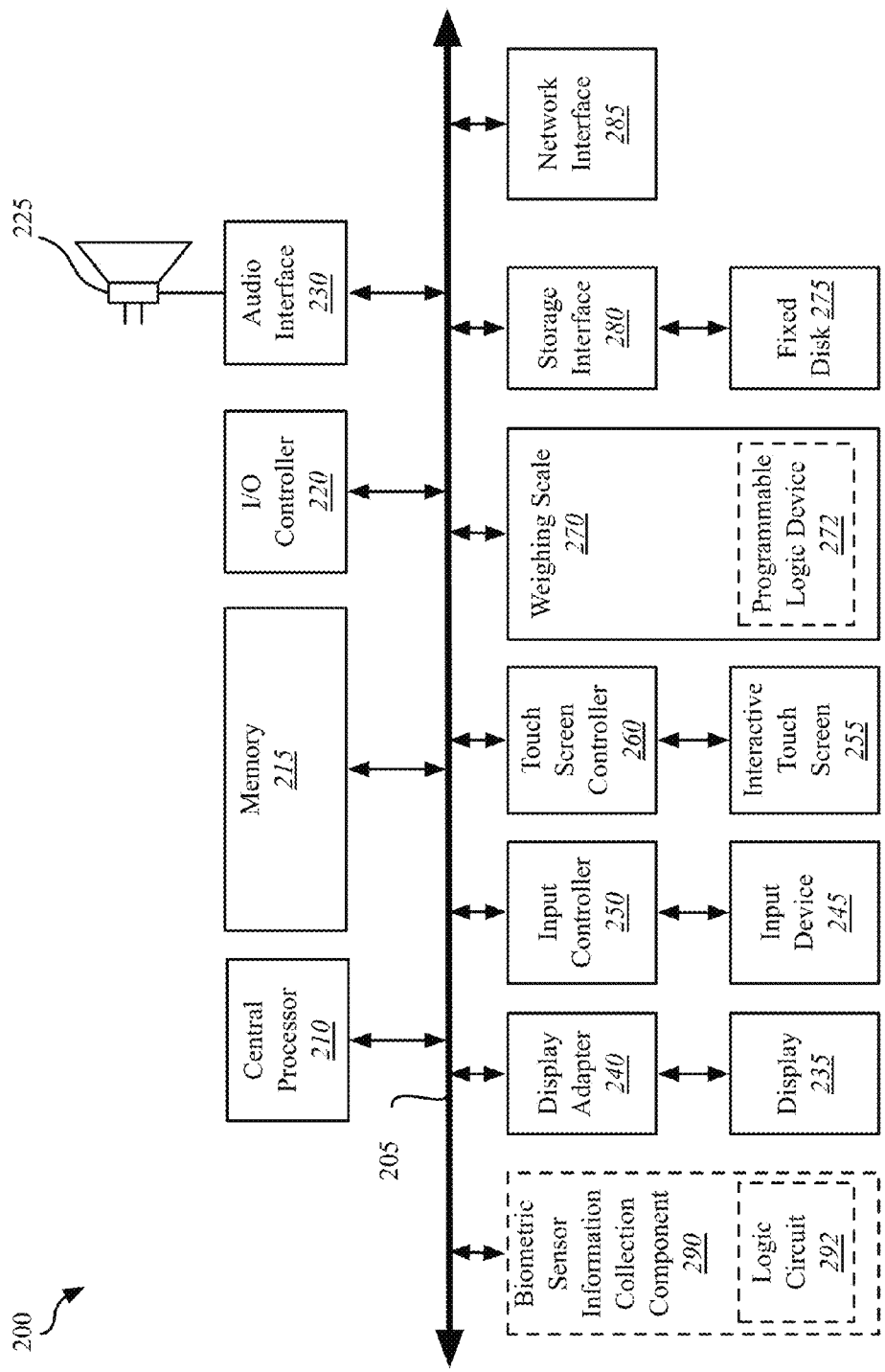
FIG. 2 is a schematic block diagram of one embodiment of an electronic configuration for one or more of the computing devices of FIG. 1.
Figure 3A:
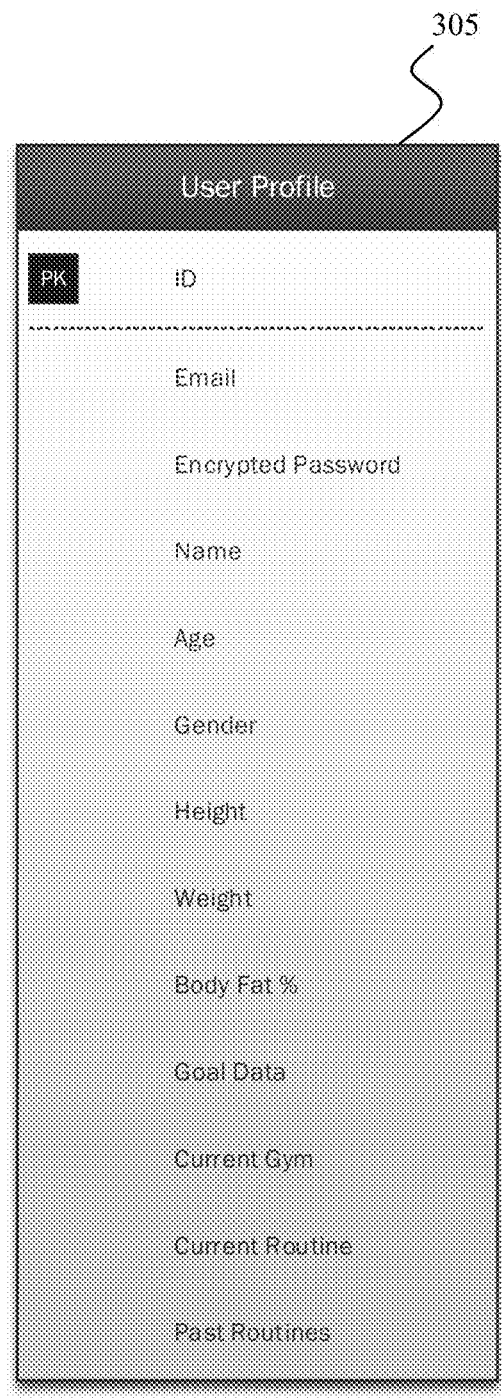
FIG. 3A through FIG. 3H are a series of diagrams of various tables stored in the relational database of FIG. 1.
Figure 3B:
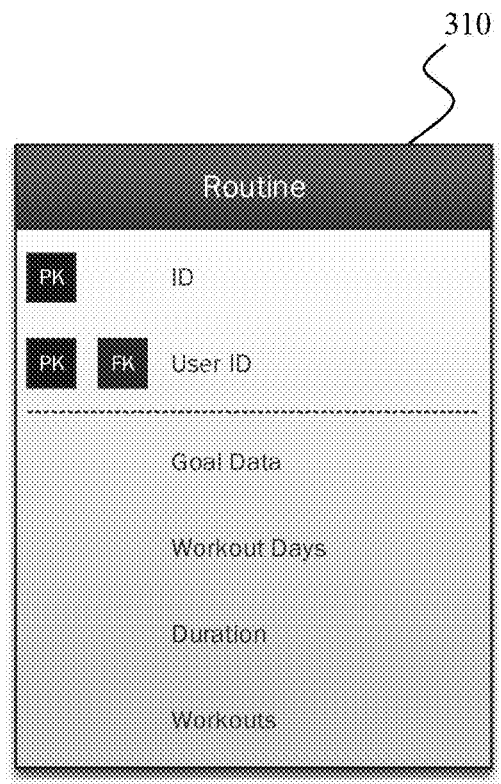
Figure 3C:
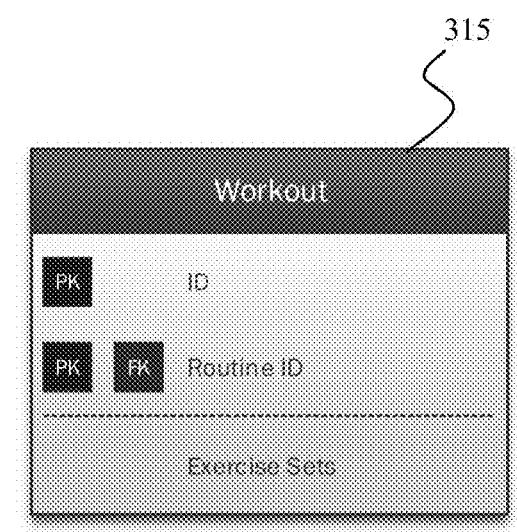
Figure 3D:
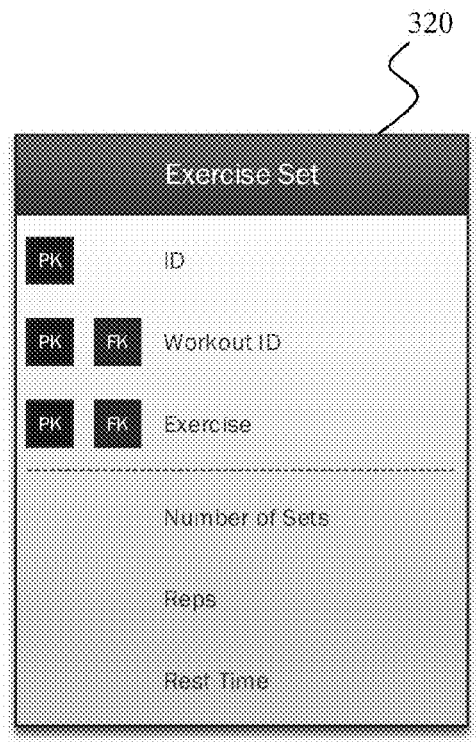
Figure 3E:
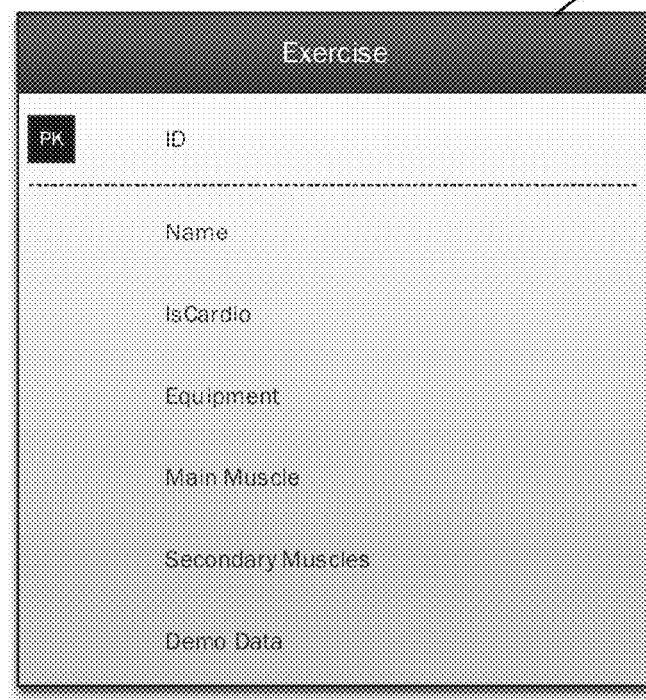
Figure 3F:
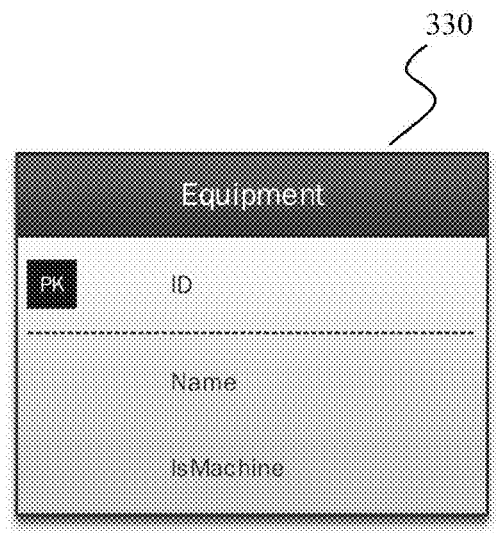
Figure 3G:
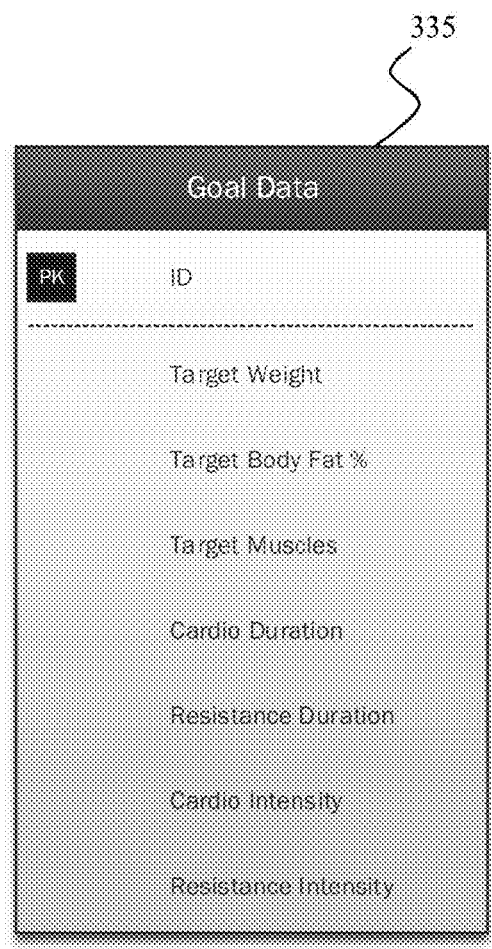
Figure 3H:
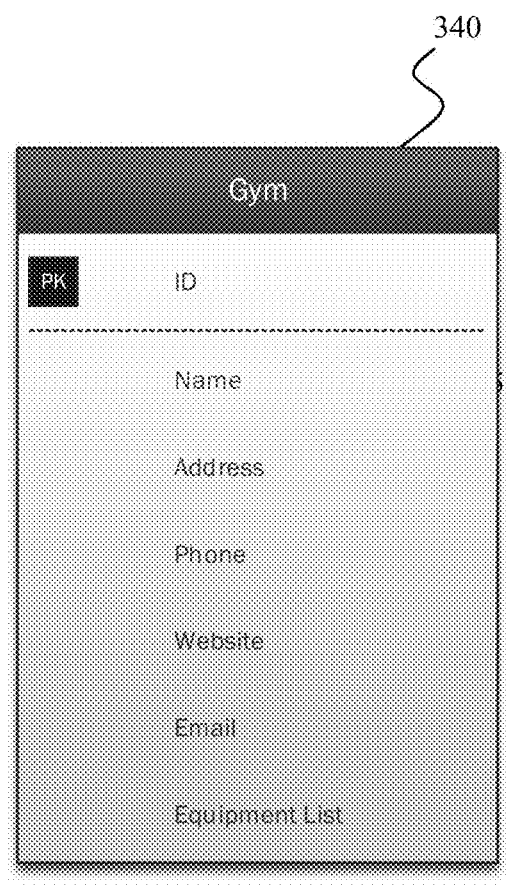
Figure 4:
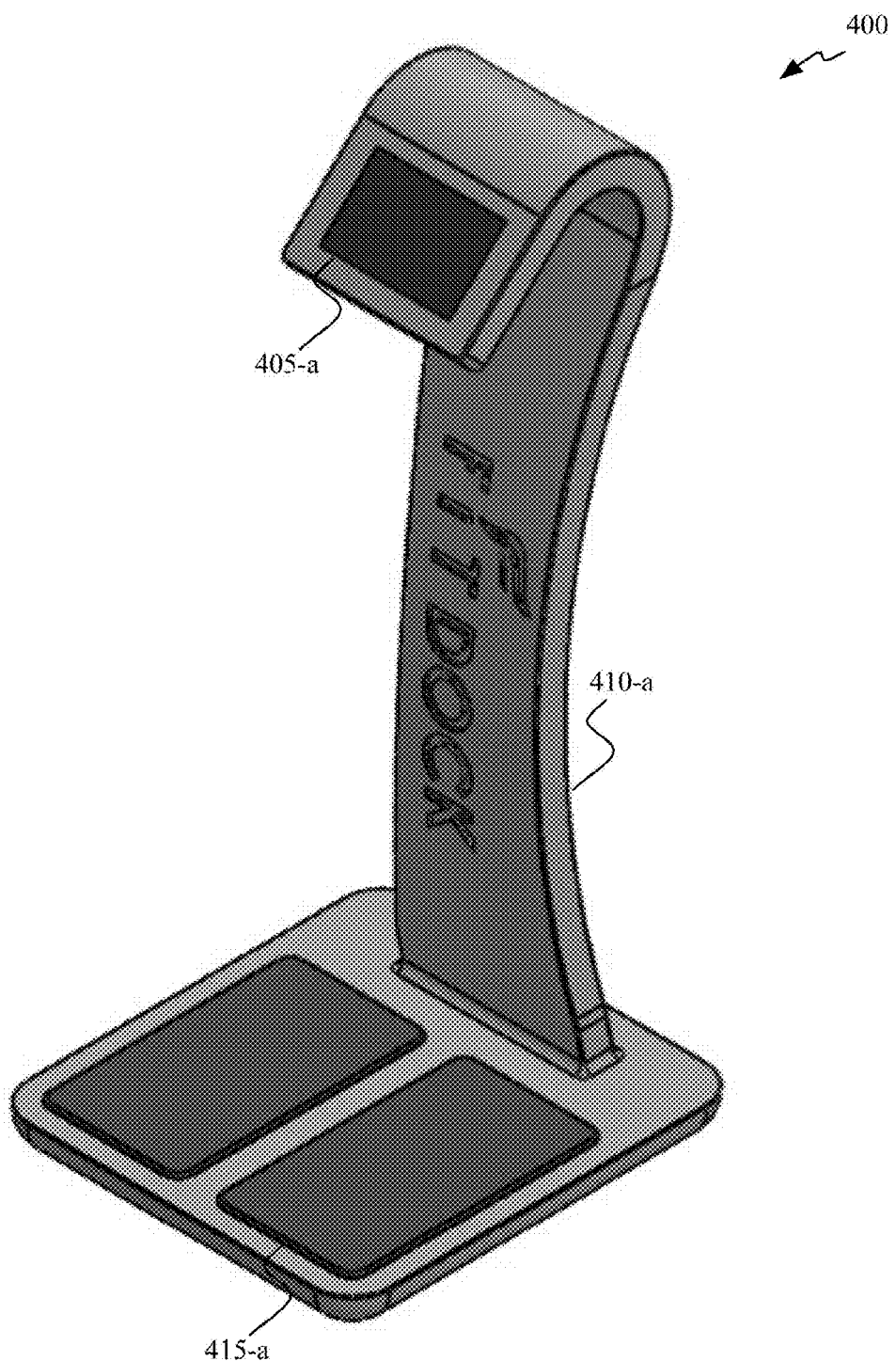
FIG. 4 is a perspective view of an automated station further described herein.
Figure 8:
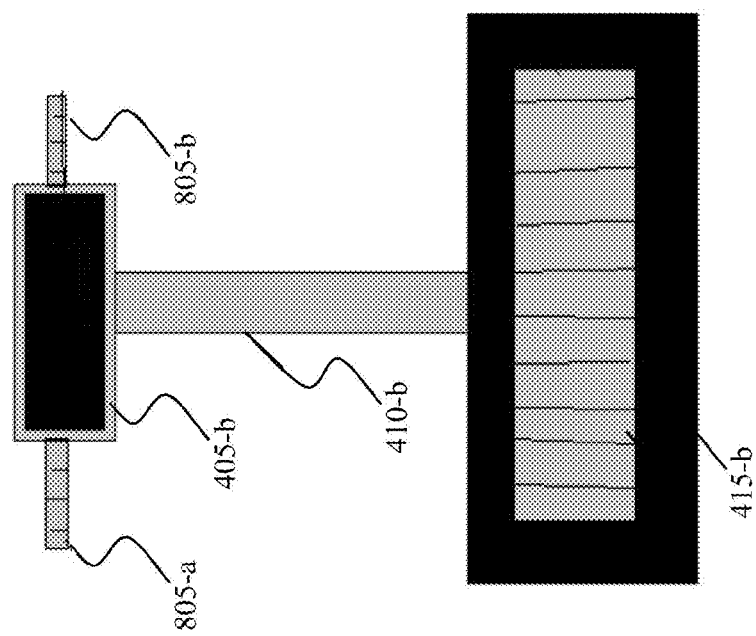
FIG. 8 is another front plan view of the automated station of FIG. 4.

Referring now to FIG. 2, device 200 is an example of one or more of the computing devices of FIG. 1. In one configuration, device 200 includes a bus 205 that interconnects major subsystems of the servers 110, 111, 115, 116 and client devices 102, such as a central processor 210, a memory 215 (typically RAM, but which may also include ROM, flash RAM, or the like), an input/output controller 220, an external audio device, such as a speaker system 225 via an audio output interface 230, an external device, such as a display screen 235 via display adapter 240, an input device 245 (e.g., a scanner interfaced with an input controller 250), an interactive touchscreen device 255 (coupled with a touchscreen controller 260), a weighing scale device 270 implementing an optional programmable logic device 272 (e.g., ASIC, FPGA or the like), an optional biometric sensor 290 implementing one or more logic circuits 292, and a storage interface 280 to a data store 275. Also included is a network interface 285 which can be coupled directly to bus 205.

In some embodiments, the interactive touchscreen 255 can include a touch-sensitive display overlay allowing player interaction with the images on the display 235. The touchscreen 255 and the touchscreen controller 260 can be connected to the display adapter 240. In certain instances, a user can make decisions and input selections into the device 200 by touching the touchscreen 255 at the appropriate places. The device 200 may further include multiple communication ports for enabling communication of the processor with external peripherals, such as external video sources, expansion buses, sensors, scanners or other displays, a SCSI port or a key pad. In some implementations, the device includes at least one weighing scale, implementing a programmable logic device 272, in communication with the central processor 210.

Bus 205 allows data communication between central processor 210 and system memory 215, which may include read-only memory (ROM) or flash memory (neither shown), and random access memory (RAM) (not shown), as previously noted. The RAM is generally the main memory into which the operating system, if any, and biosensing and automated workout generation system application programs are loaded. The ROM or flash memory may contain, among other code, the Basic Input-Output system (BIOS), which controls basic hardware operation such as the interaction with peripheral components 245, 290 or devices 270.

As with the other storage interfaces of device 200, storage interface 280 can connect to a standard computer readable medium, such as a fixed disk drive 275, for storage, retrieval of information, or both. The fixed disk 275 can be a part of device 200 or can be separate and accessed through other interface systems. Network interface 285 may provide a direct connection to a remote device via a direct network link. Network interface 285 may provide such connection using wireless techniques, including Wi-Fi, digital cellular telephone connection, digital satellite data connection, or the like.

Many other devices or subsystems (not shown) may be connected in a similar manner (e.g., displays, computing devices, keypads, cameras, authentication devices, and so on). Conversely, all of the devices shown in FIG. 2 need not be present to practice the present systems and methods. The devices and subsystems therefore may be interconnected in different ways from that shown in FIG. 2. The aspect of some operations of a system such as that shown in FIG. 2 are readily known in the art and are not discussed in detail in this application. Computer instructions to implement the present disclosure may be stored in a non-transitory computer-readable medium such as one or more of system memory 215 or data store 275.

Referring now to FIG. 3A through FIG. 3H, a series of database tables are provided supporting the various services and functions of the applications and devices of the several automated system embodiments. A User Profile table 305 contains user authentication and identification information. Goal Data, Current Gym, Current Routine, and Past Routines are referenced in corresponding tables.

The Routine table 310 defines a workout routine. It is associated with a specific user and contains a reference to the Goal Data used to create the workouts. Workout Days is an integer describing how many days out of a week the user will work out. Duration is the time in minutes for each workout. Workouts is a list of workout table references.

Workout table 315 describes the exercises for one workout day. It is associated with a routine by a Routine Table ID reference. Exercise Sets is a list of Exercise Set table entries.

The Exercise Set table 320 describes one exercise in a workout. The Workout ID associates an Exercise Set record to a single Workout record. The Exercise field references the exercise included in the Exercise Set. Number of Sets indicates how many "sets" to are to be completed as part of the workout. Reps indicates how many time to repeat the exercise for one set. Rest Time is the wait time between sets.

The Exercise table 325 describes an exercise. Name is the name of the exercise. IsCardio is a flag indicating if this is a cardio-based exercise. Equipment is a list of equipment associated with the exercise. Main Muscle is the name of the primary muscle that is used during this exercise. Secondary Muscles is a list of muscles other than the primary muscle used during the exercise. Demo Data is the location of the demonstrational videos or animation files if available.

The Equipment table 330 describes a piece of equipment in a gym. Name is the name of the equipment, and IsMachine is a flag used to indicate if this is free weight equipment or machine equipment.

Goal Data table 335 describes the data relating to a user's goals. Target Weight is the weight goal for a user. Target Body Fat % is the user's goal percentage for their body fat. Target Muscles are populated through processing goal question responses and lists of the muscles to be worked out during the routine. Cardio Duration is the duration in minutes for cardio exercises during a workout for the routine. Resistance Duration is the duration in minutes for the resistance exercises during a workout for the routine. Cardio Intensity is the intensity key for cardio exercises for this routine. Resistance Intensity is the intensity key for the resistance exercise for this routine.

The Gym table 340 describes the location, contact information, and equipment for a gym. The Equipment List references equipment from the Equipment table.

Referring now to FIG. 4 through FIG. 8, in some embodiments the automated station includes a weighing scale at the base of station 415, a support arm extending upwardly from the base 410, and an interactive touchscreen at an upper portion of the support arm 405. In some instances, the automated station also includes two electrical impedance sensors 805 extending from the stand 410 or touchscreen 405. In certain implementations, the sensors 805 are mounted in opposed handles extending laterally outwardly from opposed sides of the touchscreen 405. The automated station can include an internal computer having a microprocessor, digital memory and storage resources, the touchscreen display, and communications facilities such as an Ethernet port, a USB port, other ports if desired, and wireless Wi-Fi connectivity.

In order for the automated system to generate a personalized workout, the user will provide certain initial information to the automated system and additional information will be collected from specialized custom hardware present in the system. Data preferably supplied by the user may include, but is not necessarily limited to a username, system password, e-mail address, name, height, and sex. The user will also preferably input their body type (ectomorph, mesomorph or endomorph) by selecting one of the three images that most closely matches their own body shape. The user may then enter his or her specific goals, including but not limited to desired weight loss, muscle building, and/or hybrid. The automated system may preferably collect certain biological parameters from the user, including but not limited to heart rate, body fat percentage, weight, and the like via at least one of weighing scale device 270 and biometric sensor 290. For example and without limitation, the user's weight may be collected by weighing scale device 270 and biometric sensor 290 may comprise the electrical impedance sensors 805 that may be used to determine body fat percentage and obtain any other relevant biological data within the extent of their measurement capability. These parameters will be stored as a part of the user's profile and be available to the automated system applications for use in generating a workout recommendation for the user. In some embodiments, biometric sensor 290 may be in data transfer communication with one or more of the computing devices 200 of the automated system and data there from be utilized by an application of the automated system to generate exercise recommendations for the user (see FIG. 17).

Figure 9:
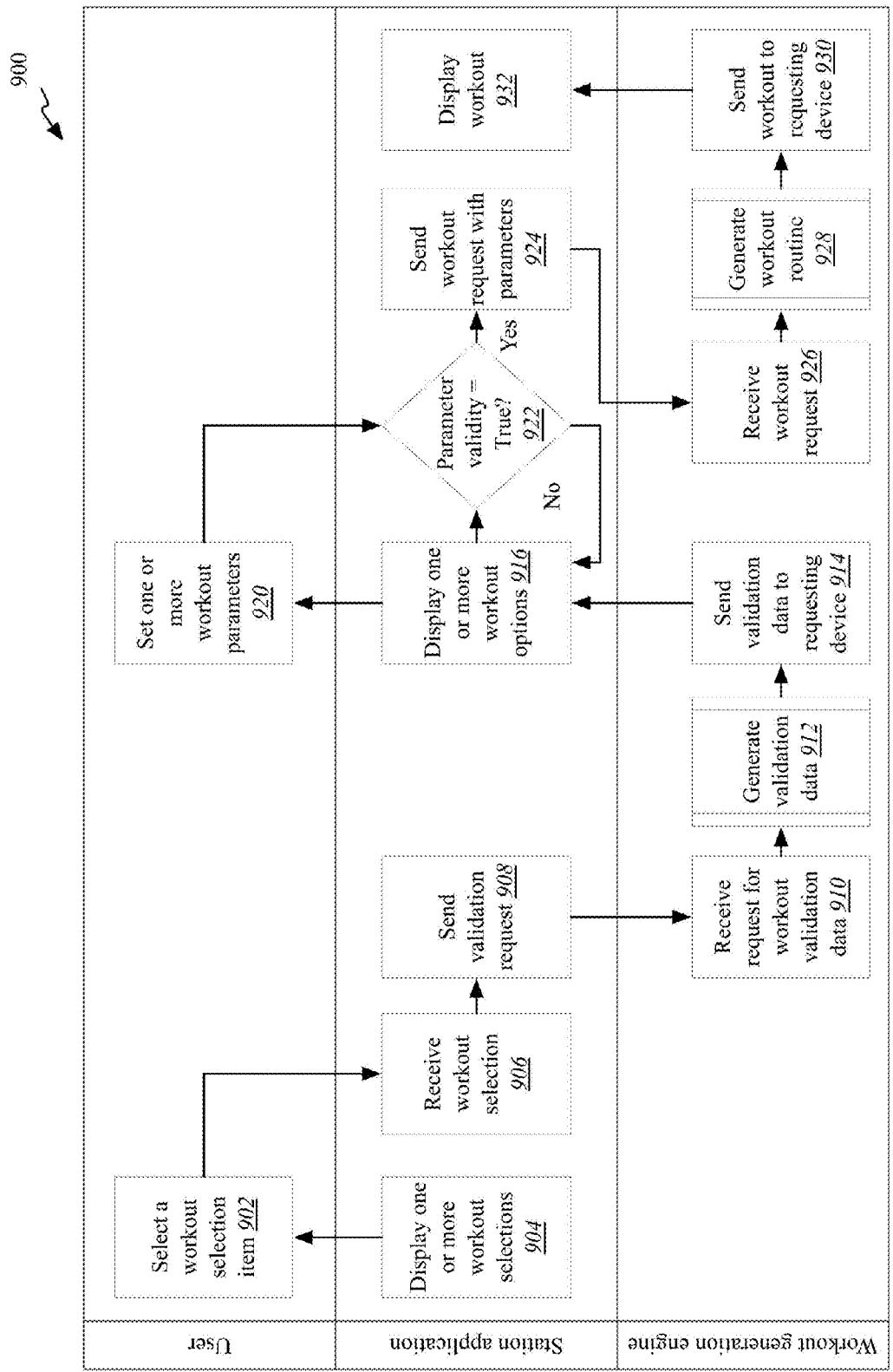
FIG. 9 is a flow diagram of a workout generation process performed by one or more components of FIG. 1.

Referring now to FIG. 9, an automated station application comprising a workout generation engine displays one or more workout selection items 904 such as, for example, a one-time workout selection item. Once the user selects a workout item 902, the automated station application sends the workout selection and a validation request to the workout generation engine 906, 908 requesting workout validation data for the current gym. Once the server receives the request 910, validation data is generated 912 and returned to the station application 914. The automated station application uses this data, at least in part, to generate one or more appropriate workout options 916. The user then sets one or more of the parameters represented by the workout options 920 to be submitted for the generation of a workout. These parameters can include, for example, the duration, a list of muscles to work out, and the workout intensity key. The automated station application then determines that there no erroneous parameters entered and that they are valid (for example, by using the duration to check the number of muscles that can be used for the duration against the number of muscles in the list and by checking to make sure the value for the Workout Intensity Key is one of the three possible values) 922. In the case of an invalid parameter, the user is prompted to make changes 916. Once all parameters are determined to be valid, the automated station application marshals the parameters into a JSON object where the key is the parameter name and the value is the selected value. The automated station application then sends a request to the server to generate a workout passing the JSON object as data 924. Upon receiving the request 926, the server executes a generate workout routine, generating the workout 928. The generated workout is then returned to the requesting automated station application as an array of JSON objects 930. Each JSON object in this array corresponds to a record in the Exercise Database with the data from the intensity table for the intensity key chosen appended. Once received, the automated station application then displays the workout 932.

In some embodiments, a JSON table indexed by the workout duration (for example, 30, 45, or 60 minutes) is returned as a table containing at least two values. These values can include an "ExerciseCount" such as the maximum number of exercise that can be generated for the selected duration and the "MuscleCount" such as the maximum number of muscles that can be exercised for the selected duration. The following is an example of a portion of the JSON object content for multiple durations:

```
{
    '30': {
        'ExerciseCount': 6,
        'MuscleCount': 3
    },
    '45': {
        'ExerciseCount': 8,
        'MuscleCount': 4
    },
    '60': {
        'ExerciseCount': 10,
        'MuscleCount': 5
    }
}
```

In some instances, a JSON object is provided including enumerated data types including, for example, "Strength", "MuscleMass" and "Endurance". These values can be used to access data from a workout intensity table stored and communicating in, for example, a JSON object. This object can include, for example, the number of repetitions per exercise set, the number exercise sets per workout, the rest periods between sets, and the like. The following is an example of a portion of the JSON object content for workout intensity JSON object:

```
{
    'Strength' : {
        'reps' : 8,
        'sets' : 3,
        'restBetweenSets' : 60
    },
    'MuscleMass' : {
        'reps' : 10,
        'sets' : 3,
        'restBetweenSets' : 45
    },
    'Endurance' : {
        'reps' : 12,
        'sets' : 3,
        'restBetweenSets' : 30
    }
}
```

In some instances, a JSON object is provided including, for example, data for use by the workout generator for the creation of one or more workouts. The following is an example of a portion of the JSON object content for a workout JSON object:

```
{
'Duration': 30,
'Muscles':[Chest, Abs, Biceps, . . . ],
'Intensity': 'Endurance'
}
```

Figure 10:
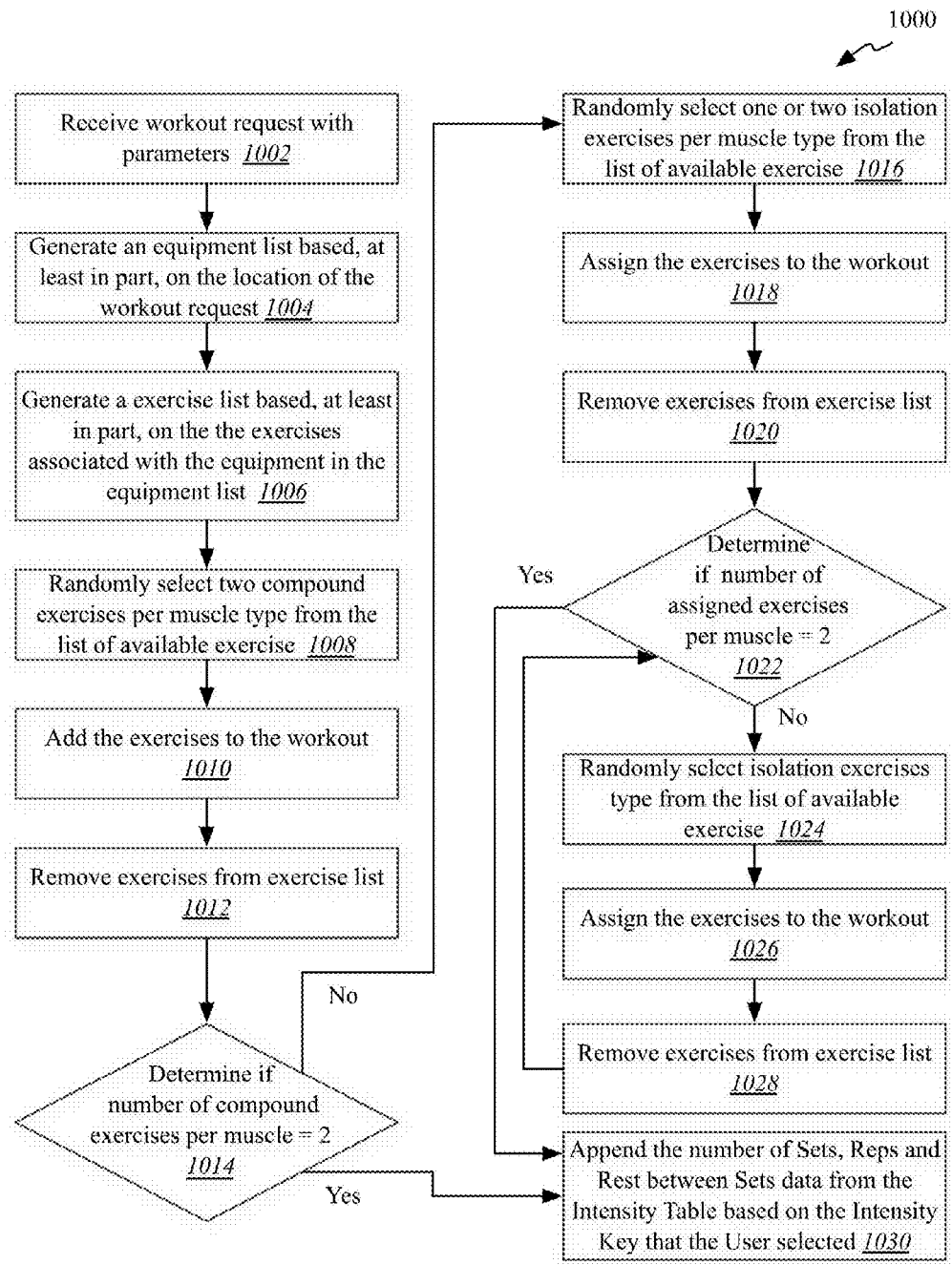
FIG. 10 is a flow diagram of a workout generation algorithm for generating workout routines in the workout generation process of FIG. 9.

Referring now to FIG. 10, a workout generation algorithm generates a workout based on parameters from the user. Once the workout generation engine comprising the workout generation algorithm receives the workout parameters 1002, it will generate an equipment list via said algorithm. In some instances, the generation of this list involves identification of equipment associated with a particular location 1004. Exercises associated with the equipment in the equipment list are retrieved and an exercise list created 1006. Two compound exercises are randomly selected added to the workout for each muscle identified in the workout data 1008, 1110. Once successfully added to the workout, the exercise is removed from the exercise list 1012.

If a muscle does not have two compound exercises assigned 1014, the workout generation engine comprising the workout generation algorithm randomly selects either one or two isolation exercise for the missing compound exercise(s) for that muscle 1016 and assign the exercises to the workout 1018. Once successfully added to the workout, the exercise is removed from the exercise list 1012. If there are still exercise slots open 1022, for each open slot the workout generation engine comprising the workout generation algorithm randomly selects a muscle and then randomly selects an isolation exercise for that muscle from the list of available exercises 1024. The exercise is assigned to the workout 1026, and once successfully added, the exercise is removed from the exercise list 1028. Once all exercise slots are filled, the workout generation engine comprising the workout generation algorithm then appends the number of sets, reps and rest between sets data from the intensity table based on the intensity key selected by the user.

Figure 11:
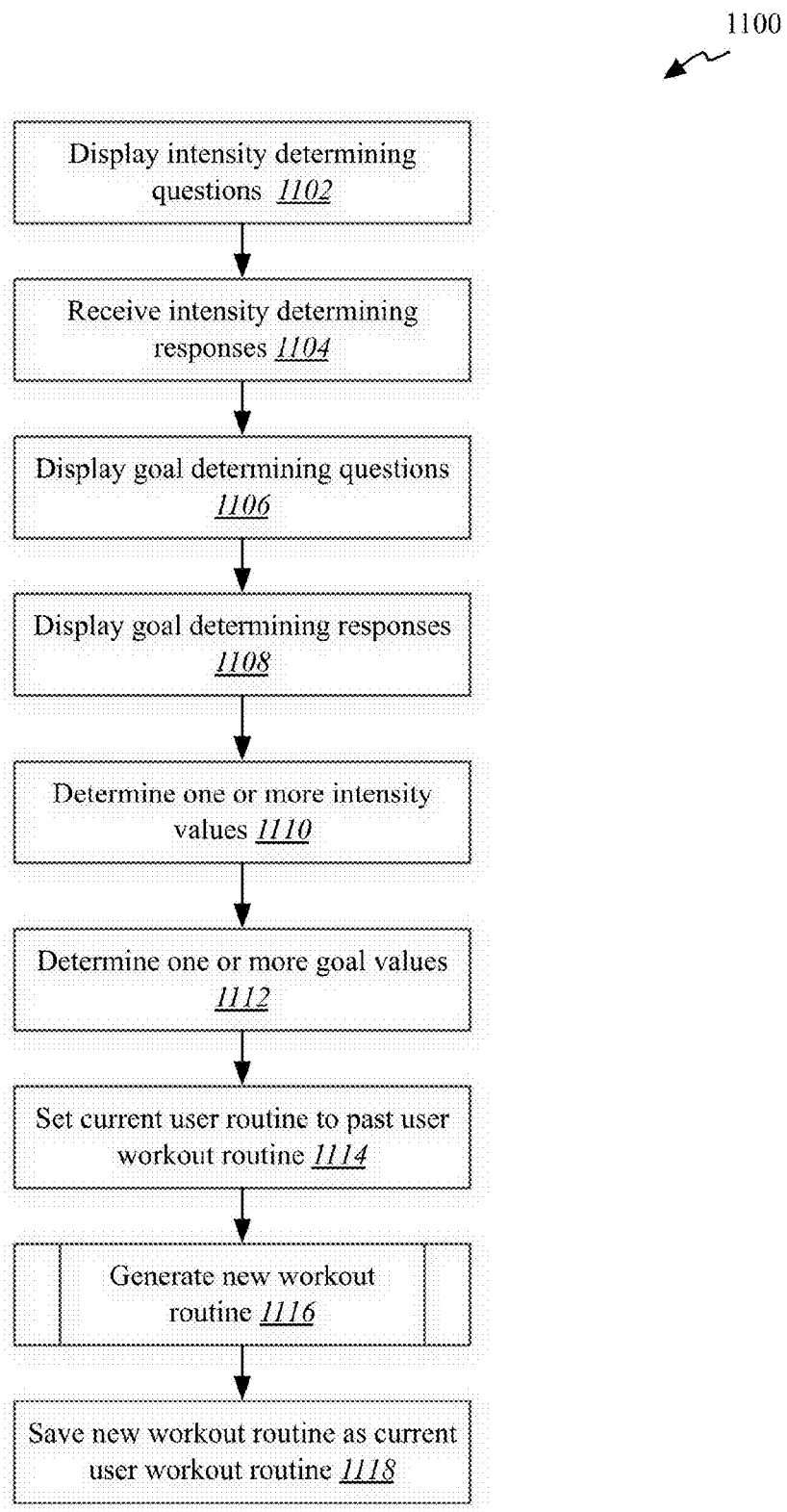
FIG. 11 is a flow diagram of a goal-based workout generation process performed by one or more components of FIG. 1.

Referring now to FIG. 11, in some embodiments, a goal based workout generation process 1100 implemented by the workout generation engine comprising the workout generation algorithm generates a workout based on goals set by the user. Initial intensity determining questions are displayed on the station application 1102. Once responses to the intensity questions are received 1104, one or more goal determining questions are displayed 1106. Responses are received by the station application 1108, and one or more intensity values, goal values, or both are determined 1110, 1112. In some instances, these questions are presented in a different order or simultaneously. The current user routine is then set to past user workout routine 1114 and a new goal-based workout is generated 1116. This workout, once generated, is saved as the current user workout routine 1118.

This goal-based workout generation process can, in some implementations, initiate at the creation of a profile or editing of user goals. In some instances, the automated station application displays a set of questions designed to determine the correct intensity for a user. These questions can be from a fixed set of questions stored in the client app, retrieved from a server, or both, and result in determination of an intensity key, the duration for each workout, and how many days in a 7 day work week will be regarded as workout days. The automated station application may then guide the user though a set of question to determine the user's goals.

In some embodiments, the goal questions are arranged in a tree-like data structure in which the leaf nodes contain the list of muscles to work out and two flags indicating if cardio exercises are to be added and if cardio exercises are added every workout or consolidated into one day. This tree is traversed using a depth first search that terminates on at the first leaf node encountered. The answers to the questions can dictate which child branch is executed. The goal and intensity data are saved in the user's profile, resulting in the current routine being saved as a past routine and replaced with a new routine. The goal-based workout generation process is then executed for the new routine using at least the goal and intensity data as inputs.

Figure 12A:
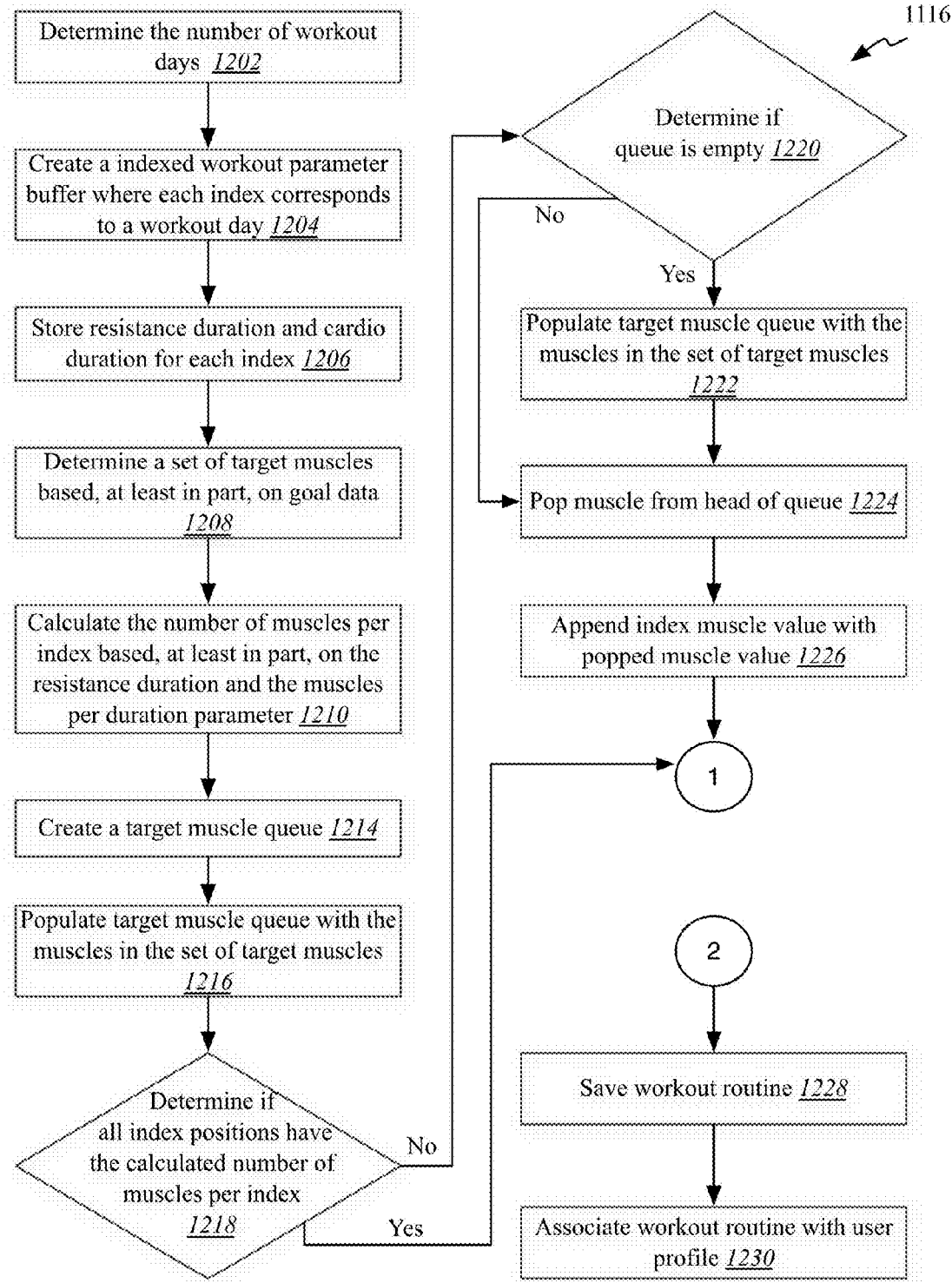
FIG. 12A and FIG. 12B comprise a flow diagram of a workout generation algorithm for generating workout routines in the goal-based workout generation process of FIG. 11.
Figure 12B:
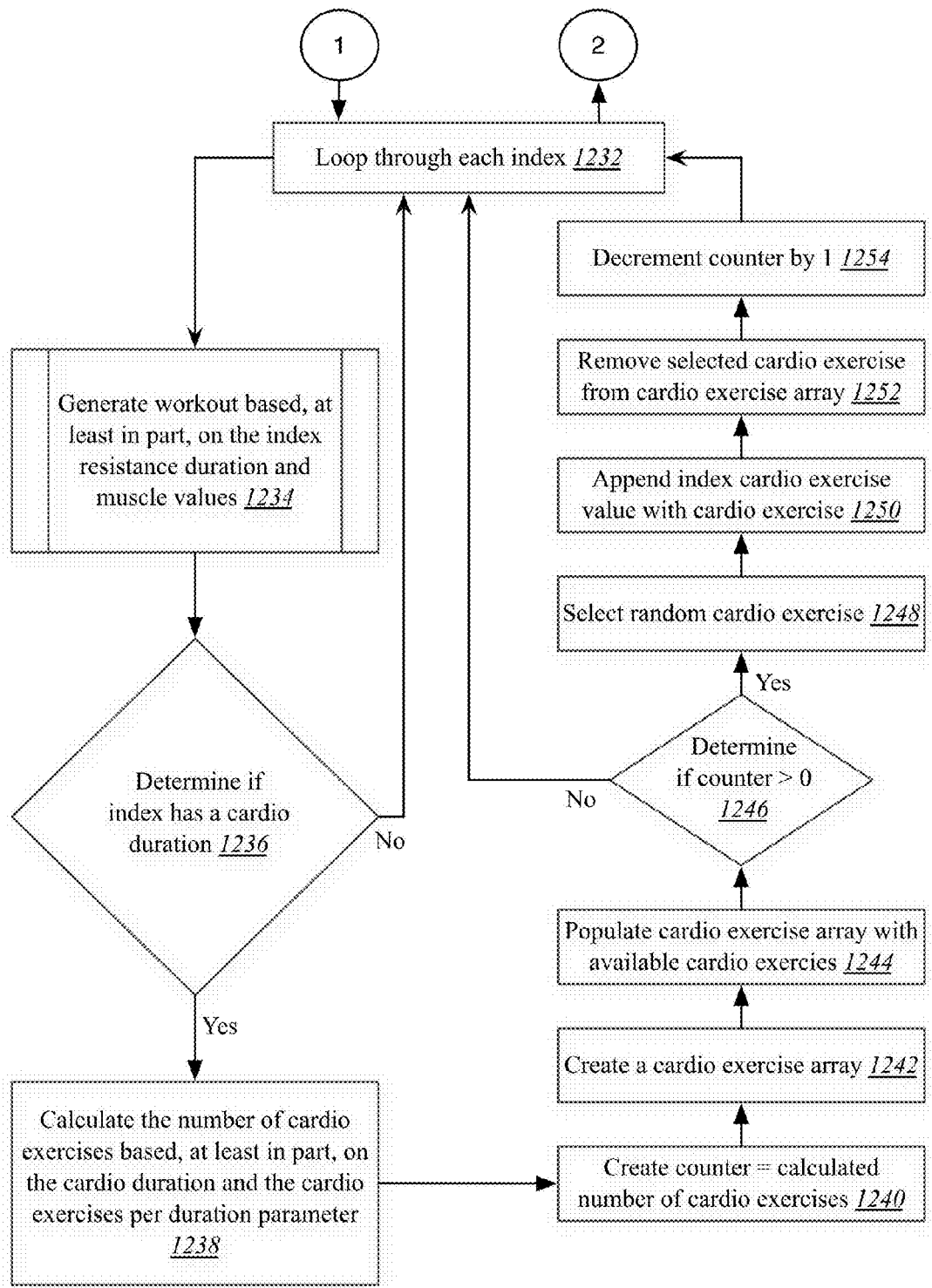

Referring now to FIG. 12A and FIG. 12B, the workout generation engine comprising the workout generation algorithm generates a workout based on a set of goals. The workout generation engine comprising the workout generation algorithm first determines the number of workout days 1202, then creates an indexed workout parameter buffer to hold the workout data 1204. The size of the buffer will correspond to the number of days to workout. Each index corresponds to one workout day. The data in each index of this buffer can include the resistance duration, cardio duration, and a list of muscles to workout 1206. The list of target muscles can be determined, at least in part, from the user goal data 1208. The target muscles from the goal data are split out over the set of days based, at least in part, on the resistance duration and the muscles per duration parameter of the workout validation data 1210. As an example, if the resistance duration is 30 minutes and the validation data says that the total number of muscles for a 30 minute workout is three, then three muscles are added to each day.

The workout generation engine comprising the workout generation algorithm creates a target muscle queue 1214, then populates the queue by copying the target muscle items in the target muscle list to the queue. A determination is made as to whether each index in the buffer has the correct number of muscle assignments per index 1218. If the determination returns false, the muscle queue is checked to ensure it has contains at least one muscle item 1220, and the muscle item at the head of the queue is dequeued 1224 and appended to the list of muscles for the index 1226. In the event the queue is empty, it is repopulated 1222 prior to initiating a dequeue event.

Once all index positions are properly assigned target muscles, each index is looped through 1232 in order to correctly populate the indexes with exercises. A workout is generated in accordance with the method 1000 of FIG. 10. For each index, a determination is made whether a cardio duration is set 1236. If so, the workout generation engine comprising the workout generation algorithm will select a random cardio exercise 1248. The random selection process can involve the creation of a cardio exercise array 1242 populated with the cardio exercises 1244 and a counter corresponding to the number array positions 1240, through which the number of positions is calculated, at least in part, by assessing the cardio duration and the cardio exercises per duration parameter 1238. So long as the counter is not empty 1246, the random cardio exercise is selected 1248 and the cardio exercise value for the index is appended with the selected cardio exercise 1250. Once the appending is successful, the cardio exercise is removed from the array 1252 and the counter is decremented by one 1254. In some embodiments, duplicate cardio exercises are not appended to a single day index position. After exercise assignments are complete for all days, the workout routine is saved 1228 and associated with the user profile 1230.

Figure 13:
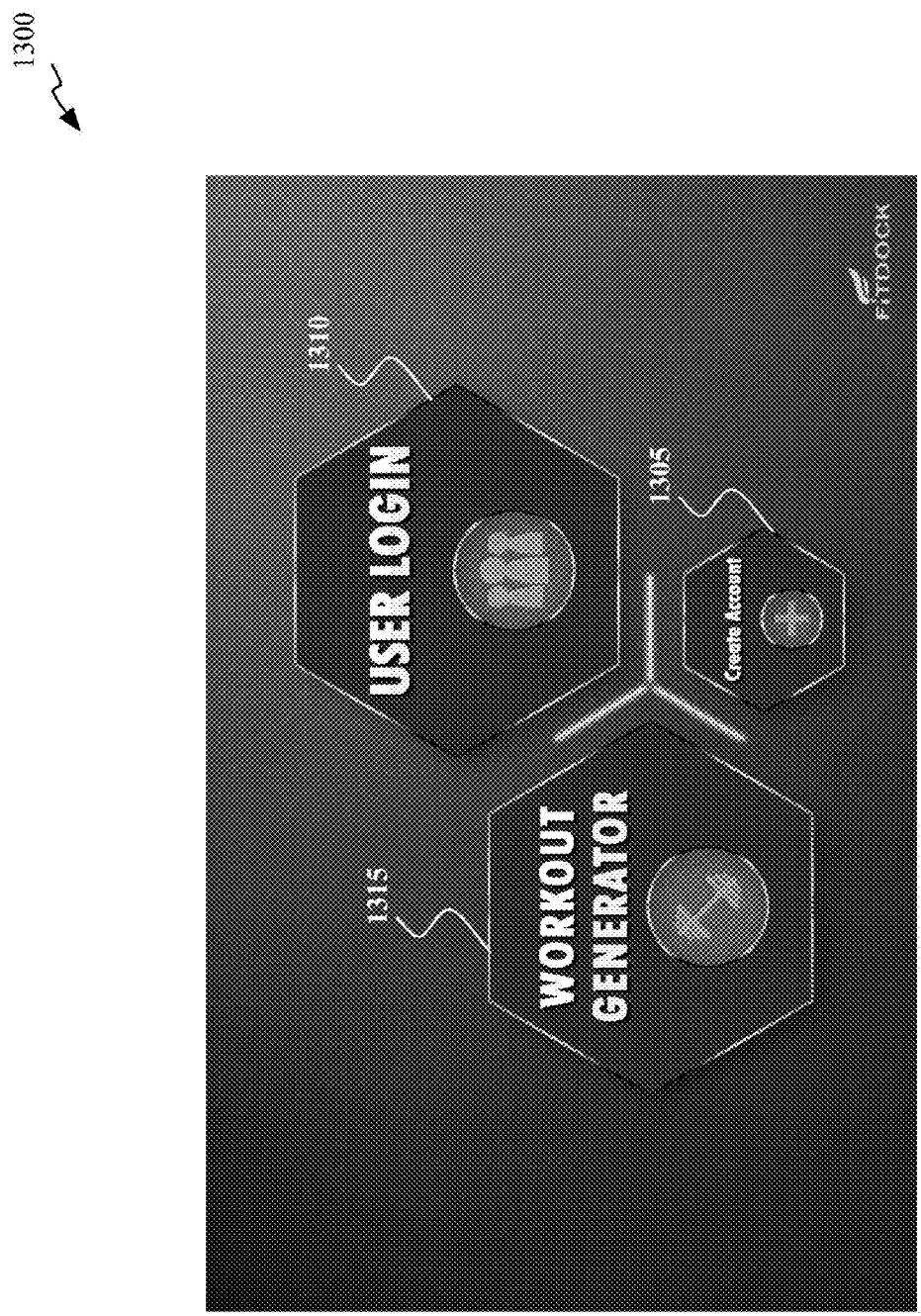
FIG. 13 is a screen capture of the introductory view displayed by the interactive touchscreen of the automated station of FIG. 4.

Referring now to FIG. 13, an introductory view is displayed on the station display where a user can create an account by selecting the create account button 1305, login to an existing account by selecting the user login button 1310, or generate a one-time workout without creating or accessing a user account or user profile by selecting the workout generator button 1315.

Figure 14:
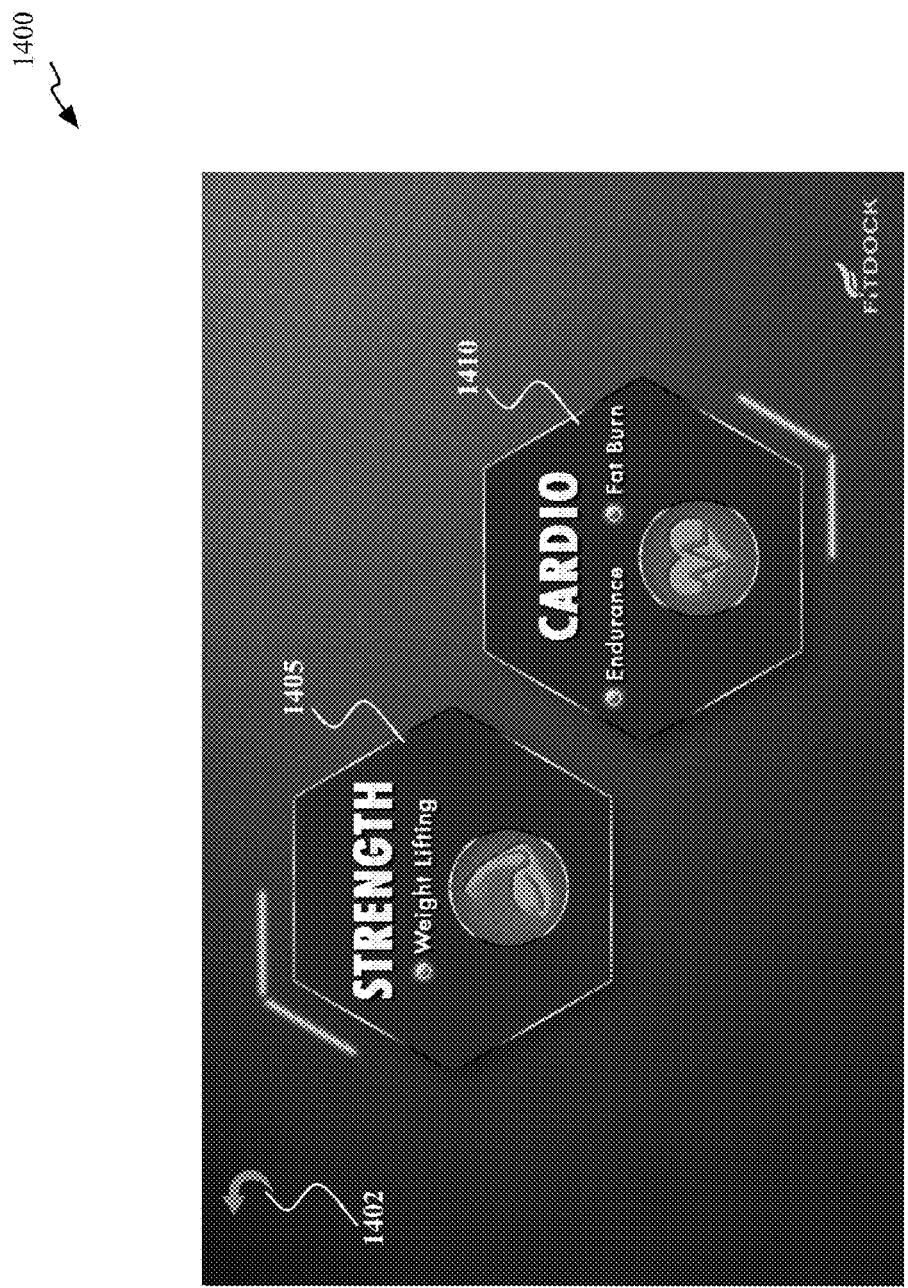
FIG. 14 is a screen capture of the one-time workout view displayed by the interactive touchscreen of the automated station of FIG. 4.

Referring now to FIG. 14, selecting the workout generator button displays the one-time workout view 1400. This view can include a back button in the upper left corner 1402 that will direct the application to display the introductory view. There is also a strength button 1405 for generating a resistance workout and a cardio button 1410 for generating cardio workout.

Figure 15:
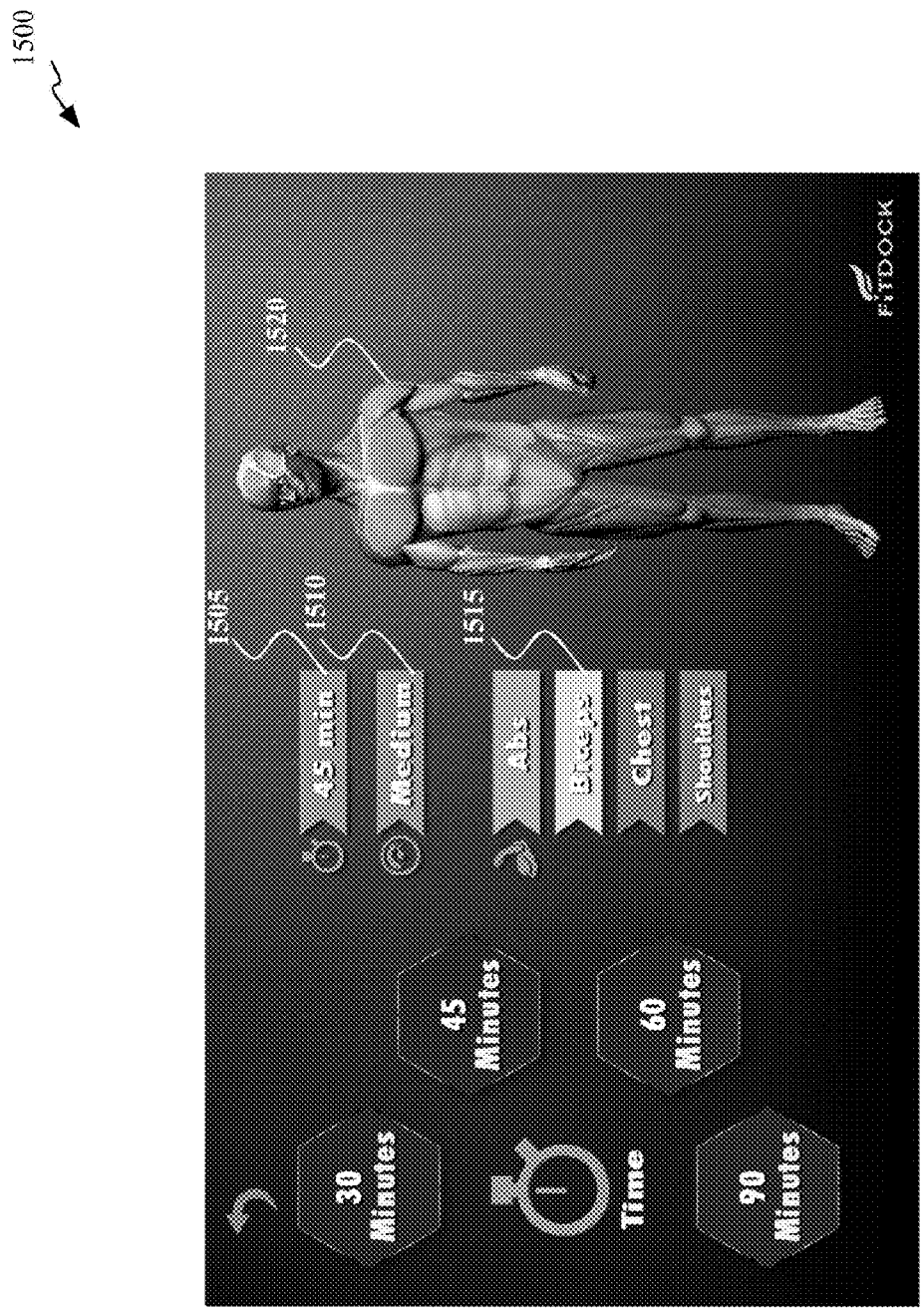
FIG. 15 is a screen capture of the workout parameters view displayed by the interactive touchscreen of the automated station of FIG. 4.

Referring now to FIG. 15, a workout parameters view 1500 receives different settings for use in workout generation algorithms. This can include setting the total duration of the workout, setting the intensity of the workout, and setting the muscle groups for the workout. In some embodiment, an anatomical graphic is displayed animating the different muscles and highlighting muscles to be exercised in this workout.

Figure 16:
FIG. 16 is a screen capture of the user profile view displayed by the interactive touchscreen of the automated station of FIG. 4.

Referring now to FIG. 16, a user profile view 1600 displays the values and controls associated with the user profile. In some embodiments, the hexagon buttons 1605, 1610, 1615, 1620 to the left will animate in a circle as the user scrolls though the different options. Selecting a hexagon button populates the data display area on the right with stored data associated with the button selection event.

Figure 17:
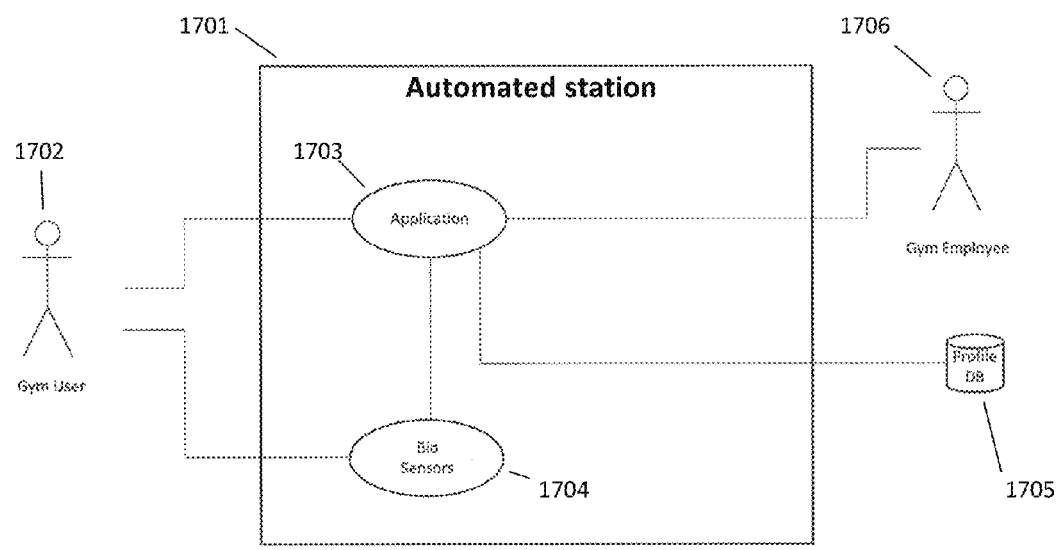
FIG. 17 depicts the interaction of certain devices or components operating within the computer network or similar digital processing environment of FIG. 1.

FIG. 17 depicts the interaction and cooperation between devices or components in some embodiments of the automated system operating within the computer network or similar digital processing environment of FIG. 1. Here, user 1702 interacts with one or more automated system applications 1703 running in automated station 1701 for various purposes, including but not limited to providing user profile data or receiving workout recommendations. As disclosed elsewhere herein, these applications may be running in whole or in part, in addition to or as an alternative to running on automated station 1701, on any other suitable computing device within said environment. Biosensors 1704, which may comprise at least one of any of the biometric sensors 290 and the electrical impedance sensors 805, are in data retrieval communication with user 1702 for the purpose of obtaining physical or biometric data. Biosensors 1704 are also in communication with automated system application 1703, which in turn is in communication with profile database 1705 for the purpose of storing and retrieving data obtained from user 1702 and biosensors 1704 for use by the automated system, including but not limited to use in generating workout recommendations for user 1702. Gym employee 1706 is also capable of interacting with application 1703 for any necessary purpose, including but not limited to administrative, troubleshooting, or maintenance functions.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures may be implemented to achieve the same functionality.

The process parameters and sequence of steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The various illustrative blocks, components, and engines described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

Furthermore, while various embodiments have been described and/or illustrated herein in the context of fully functional computing systems, the functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Feature implementing functions may also be physically located at various positions, including being distributed such that portions of functions are implemented at different physical locations.

Unless otherwise noted, the terms "a" or "an," as used in the specification and claims, are to be construed as meaning "at least one of". Thus, for example, a list of "at least one of A, B, or C" means A or B or C or AB or AC or BC or ABC (i.e., A and B and C).

In addition, for ease of use, the words "including" and "having," as used in the specification and claims, are interchangeable with and have the same meaning as the word "comprising." In addition, the term "based on" as used in the specification and the claims is to be construed as meaning "based at least upon." Also, the term "immediately" with respect to a delay of machine action means without delay typically perceivable by human users.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

What is claimed is:

1. A method for providing customized exercise workout routines for a user based on new or updated goals specified by the user, the method comprising steps of:
   A. creating a new user profile or accessing an existing user profile, wherein either said user profile is associated with a particular user;
   B. obtaining, from said user, new or updated initial information pertaining to the user;

C. electronically receiving or determining the location of the user;
D. electronically receiving or determining the location and features of exercise machines or exercise apparatuses at more than one facility within the geographic locale of said user's location;
E. providing, to the user, a weighing scale and two or more electrical sensors;
F. measuring, using the weighing scale, the user's weight;
G. measuring, using voltage and current associated with the two or more electrical sensors in communication with the user's body, the user's body fat percentage;
H. storing, in the user profile associated with that particular user, at least a portion of said initial information, said user's measured weight and said user's measured body fat percentage;
I. (i) presenting, to the user, one or more questions regarding exercise workout goals of the user, (ii) receiving, from the user, responses to said one or more questions regarding the user's exercise workout goals, and (iii) storing, in the user profile associated with that particular user, said responses to said one or more questions regarding the user's exercise workout goals;
J. providing the stored user profile associated with that particular user and said location and features of exercise machines or exercise apparatuses at more than one facility within the geographic locale of said user's location to a workout generation engine;
K. receiving, from said workout generation engine, a new customized exercise workout routine based on the data stored in the user profile associated with that particular user, said exercise workout routine customized to use exercise machines or exercise apparatuses selected by said workout generation engine from those exercise machines or exercise apparatuses provided to said workout generation engine; and
L. providing, to the user, details of the new customized goal-based exercise workout routine and the location of said selected exercise machines or exercise apparatuses within the geographic locale of said user's location;
wherein method steps A-L are completed prior to the user performing any exercises associated with the method.

2. The method of claim 1 wherein the user profile comprises at least one of any of an e-mail address, an encrypted password, the user's name, age, height, measured weight, sex, measured body fat percentage, goal data, current gym, current exercise workout routine, and past exercise workout routines.

3. The method of claim 1 wherein the one or more questions regarding the user's exercise workout goals comprise at least one of any of initial intensity determining questions and goal determining questions.

4. The method of claim 1 wherein the user's exercise workout goals comprise information pertaining to at least one of any of weight loss, muscle building, a combination of weight loss and muscle building, a target weight, a target body fat percentage, target muscle building, cardio duration, resistance duration, cardio intensity, and resistance intensity.

5. The method of claim 1 wherein step I further comprises a first additional step of presenting, to the user, an opportunity to select one or more muscles to exercise from a list of muscles, a second additional step of receiving, from the user, a selection of said one or more muscles to exercise, and a third additional step of storing said selection of one or more muscles to exercise in the user profile associated with that particular user.

6. The method of claim 1 wherein (i) step J further comprises an additional step of storing, in the user profile associated with a particular user, any present exercise workout routine in said user profile as a past exercise workout routine, and (ii) step J further comprises an additional step of storing, in said user profile, the new customized goal-based exercise workout routine as the current exercise workout routine.

7. A method for generating an exercise workout to be performed at a particular location, the method comprising steps of:
A. electronically determining or receiving the location of a user;
B. receiving a workout generation request from said user and generating and storing a list comprising data of more than one exercise facilities and their locations within the geographic locale of said user's location, data of exercise equipment located at said more than one facilities, and data of the features of said exercise equipment located at said more than one facilities;
C. obtaining, from the user, new or updated initial information pertaining to the user;
D. storing said new or updated initial information;
E. providing, to the user, a weighing scale and two or more electrical sensors;
F. measuring, using the weighing scale, the user's weight;
G. measuring, using voltage and current associated with the two or more electrical sensors in communication with the user's body, the user's body fat percentage;
H. storing said user's measured weight and said user's measured body fat percentage;
I. providing, to said user, a list of workout parameters and receiving, from said user, one or more selected workout parameters from said list of workout parameters, wherein said selected workout parameters comprise at least a list of one or more muscles to work out;
J. generating, using said at least one equipment list, said user's measured weight, said user's measured body fat percentage, and said selected workout parameters, a list of exercises available to be performed using exercise equipment located at any of said more than one facilities within the geographic locale of said user's location;
K. randomly selecting, from said list of available exercises, two exercises for each muscle from said list of one or more muscles and generating an exercise workout routine by adding each of said randomly selected exercises to said exercise workout routine;
L. removing, from said list of available exercises, said two randomly selected exercises for each muscle from said list of one or more muscles; and
M. providing, to the user, said generated exercise workout routine, said list of exercise facilities and their locations within the geographic locale of said user's location, and said list of exercise equipment located at said exercise facilities available to perform said generated exercise workout routine;
wherein method steps A-M are completed prior to the user performing any exercises associated with the method.

8. The method of claim 7 wherein step A comprises determining the location of the user via GPS.

9. The method of claim 7 further comprising additional steps of (i) randomly selecting an additional muscle from said list of muscles to work out, (ii) randomly selecting an additional exercise for that muscle from said list of available exercises, (iii) adding said additional exercise to the exercise workout routine, and (iv) removing said additional exercise from the list of available exercises.

10. The method of claim 9 wherein the parameters selected by the user in step I further comprise selection of an exercise workout duration and wherein the steps of (i) randomly selecting an additional muscle from said list of muscles to work out, (ii) randomly selecting an additional exercise for that muscle from said list of available exercises, (iii) adding said additional exercise to the exercise workout routine, and (iv) removing said additional exercise from the list of available exercises are repeated until a number of muscles have been selected to fill all available time in said selected exercise workout duration.

11. The method of claim 7 wherein the parameters selected in step I further comprise an exercise workout intensity key and wherein said method further comprises an additional step of appending a number of exercise sets, exercise repetitions, and periods of rest between exercise sets to the exercise workout routine based on the selected exercise workout intensity key.

12. The method of claim 7 further comprising a step of providing, to the user, one or more goal determining questions and receiving, from the user, responses to said one or more goal determining questions, wherein said responses are used at least in part to determine at least one of any of the intensity of an exercise workout routine, the duration of an exercise workout routine, and how many days per week an exercise workout routine will be performed.

13. The method of claim 12 wherein step K of generating an exercise workout routine comprises generating a goal-based exercise workout routine by using, at least in part, the goal and intensity data as inputs.

14. A method for location-based exercise resource management, the method comprising steps of:
   A. providing a scanner and using said scanner to scan labels, other indicia, or physical or other features of exercise machines and other exercise apparatuses to identify said machines and apparatuses and their features;
   B. storing a list of said identification and features of exercise machines and other exercise apparatuses disposed at more than one facility in association with location and facility information of said machines and apparatuses;
   C. for a particular user, creating a new user profile or accessing an existing user profile associated with said user;
   D. obtaining, from said user, new or updated initial information pertaining to the user;
   E. providing, to the user, a weighing scale and two or more electrical sensors;
   F. measuring, using the weighing scale, the user's weight;
   G. measuring, using voltage and current associated with the two or more electrical sensors in communication with the user's body, the user's body fat percentage;
   H. storing, in said new or existing user profile associated with that particular user, said user's measured weight and said user's measured body fat percentage;
   I. obtaining, from the user, one or more new or updated exercise workout option(s) selected by said user;
   J. storing, in said user profile associated with the user, said initial information and said one or more exercise workout option(s) selected by said user;
   K. electronically receiving or determining the location of the user and retrieving, from the stored list of identification and features of exercise machines and other exercise apparatuses, the location, identification, and features of exercise machines and other exercise apparatuses within the user's geographic locale;
   L. providing, to a workout generation engine, (i) the location of the user, (ii) said identification, features, and location of exercise machines and other exercise apparatuses within the user's geographic locale, and (iii) said user profile;
   M. receiving, from said workout generation engine, a new exercise workout routine specific to said exercise machines and other exercise apparatuses within the user's geographic locale; and
   N. providing, to said user, said exercise workout routine and the location and facility information of said exercise machines and other exercise apparatuses associated with said exercise workout routine;
wherein method steps A-N are completed prior to the user performing any exercises associated with the method.

15. The method of claim 14 wherein (i) said workout generation engine comprises a workout generation algorithm, (ii) said one or more new or updated exercise workout option(s) selected by said user comprise a list of one or more muscle(s) to work out, and (iii) said workout generation algorithm generates the new exercise workout routine by selecting, from said stored features of the exercise machines and apparatuses, one or more exercises associated with each muscle on said list of one or more muscle(s) to work out and adding said exercises to the new exercise workout routine.

16. The method of claim 14 further comprising additional method steps of:
   A. presenting, to the user, one or more questions regarding exercise workout goals of the user;
   B. receiving, from the user, responses to the one or more questions regarding the user's exercise workout goals;
   C. storing said responses to the one or more questions regarding the user's exercise workout goals in the user's user profile; and
   D. further providing to said workout generation engine said stored responses regarding the user's exercise workout goals for use in generating an exercise workout routine.

17. The method of claim 14 further comprising a step of storing, in the user profile as a past exercise workout routine, any current exercise workout routine in the user profile and a step of storing, in the user profile as a current exercise workout routine, said new exercise workout routine.

18. The method of claim 1 wherein step B comprises determining the location of the user via GPS.

19. The method of claim 12 wherein said one or more goal determining questions and responses are directed to at least one of any of the goals of weight loss, muscle building, a combination of weight loss and muscle building, a target weight, a target body fat percentage, target muscle building, cardio duration, resistance duration, cardio intensity, and resistance intensity.

20. The method of claim 16 wherein said one or more questions and responses regarding exercise workout goals of the user are directed to at least one of any of the goals of weight loss, muscle building, a combination of weight loss and muscle building, a target weight, a target body fat percentage, target muscle building, cardio duration, resistance duration, cardio intensity, and resistance intensity.

* * * * *